US012788800B2

(12) United States Patent
Kim et al.

(10) Patent No.: US 12,788,800 B2
(45) Date of Patent: Nov. 10, 2026

(54) COMPOSITION COMPRISING GLUCAGON AND GLP-1 AND GIP RECEPTOR DUAL AGONIST AND THERAPEUTIC USE OF SAME

(71) Applicant: HANMI PHARM. CO., LTD., Hwaseong-si (KR)

(72) Inventors: Jung Kuk Kim, Hwaseong-si (KR); Jong Suk Lee, Hwaseong-si (KR); A Ram Lee, Hwaseong-si (KR); Joo Young Dong, Hwaseong-si (KR)

(73) Assignee: HANMI PHARM. CO., LTD., Hwaseong-si (KR)

(*) Notice: Subject to any disclaimer, the term of this patent is extended or adjusted under 35 U.S.C. 154(b) by 1193 days.

(21) Appl. No.: 17/766,137

(22) PCT Filed: Oct. 5, 2020

(86) PCT No.: PCT/KR2020/013467

§ 371 (c)(1),
(2) Date: Apr. 1, 2022

(87) PCT Pub. No.: WO2021/066600

PCT Pub. Date: Apr. 8, 2021

(65) Prior Publication Data

US 2023/0000950 A1 Jan. 5, 2023

(30) Foreign Application Priority Data

Oct. 4, 2019 (KR) ........................ 10-2019-0123250

(51) Int. Cl.

| | |
|---|---|
| ***A61K 38/17*** | (2006.01) |
| ***A61K 38/22*** | (2006.01) |
| ***A61K 38/26*** | (2006.01) |
| ***A61K 47/60*** | (2017.01) |
| ***A61K 47/68*** | (2017.01) |
| ***A61P 3/00*** | (2006.01) |
| ***C07K 14/605*** | (2006.01) |

(52) U.S. Cl.

CPC .............. *A61K 38/26* (2013.01); *A61K 47/60* (2017.08); *A61K 47/68* (2017.08); *A61P 3/00* (2018.01)

(58) Field of Classification Search

CPC ........ A61K 38/26; A61K 47/60; A61K 47/68; A61K 47/6889; A61K 38/1709; A61K 38/1796; A61K 38/2278; A61P 3/00; C07K 14/605

See application file for complete search history.

(56) References Cited

U.S. PATENT DOCUMENTS

| | | | | |
|---|---|---|---|---|
| 9,474,780 | B2 * | 10/2016 | Bokvist | A61P 43/00 |
| 2012/0288511 | A1 | 11/2012 | Dimarchi | |
| 2015/0164995 | A1 | 6/2015 | Kadereit et al. | |
| 2015/0166627 | A1 | 6/2015 | Kadereit et al. | |
| 2018/0186853 | A1 * | 7/2018 | Kim | A61P 3/00 |
| 2021/0338779 | A1 * | 11/2021 | Kim | A61K 31/513 |

FOREIGN PATENT DOCUMENTS

| | | | |
|---|---|---|---|
| EP | 3479841 | A2 | 5/2019 |
| KR | 10-1382593 | B1 | 4/2014 |
| KR | 10-2016-0079875 | A | 7/2016 |
| KR | 10-2019-0092343 | A | 8/2019 |
| WO | 2013164483 | A1 | 11/2013 |
| WO | 2014192284 | A1 | 12/2014 |
| WO | 2016111971 | A1 | 7/2016 |

OTHER PUBLICATIONS

Cornier et al., The metabolic syndrome, Endo. Rev. 29:777-822 (2008) (Year: 2008).*
Wu et al., "Diabetic dyslipidemia," metabolism clinical and experimental 63:1469-1479 (2014) (Year: 2014).*
Chalasani et al., "The Diagnosis and Management of Non-Alcoholic Fatty Liver Disease: Practice Guideline by the American Association for the Study of Liver Diseases, American College of Gastroenterology, and the American Gastroenterological Association," Hepatology 55:2005-2023 (2012) (Year: 2012).*
Yampolsky et al "The exchangeability of amino acids in proteins." Genetics 170:1459-1472 (2005) (Year: 2005).*
Drumm et al, Genetic Variation and Clinical Heterogeneity in Cystic Fibrosis, Annu. Rev. Pathol. Mech. Dis., 2012, 7, pp. 267-282 (Year: 2012).*
Lilly patent notice , accessed Jul. 22, 2025 at URL lilly.com/patents, 2 pages (2025) (Year: 2025).*
Merck Manual, "Alcoholic Liver Disease", at URL merckmanuals.com/home/liver_and_gallbladder_disorders/alcoholic_liver_disease/alcoholic_liver_disease.html accessed Feb. 26, 2015 (Year: 2015).*
Merck Manual, "overview of hepatitis", at URL merckmanuals.com/home/liver_and_gallbladder_disorders/hepatitis/overview_of_hepatitis.html?qt=hepatitis&alt=sh accessed Feb. 26, 2015 (Year: 2015).*
Merck Manual, "cirrhosis of the liver", at URL merckmanuals.com/home/liver_and_gallbladder_disorders/fibrosis_and_cirrhosis_of_the_liver/cirrhosis_of_the_liver.html?qt=cirrhosis&alt=sh accessed Feb. 26, 2015 (Year: 2015).*
Merck Manual, "primary liver cancers", at URL merckmanuals.com/home/liver_and_gallbladder_disorders/tumors_of_the_liver/primary_liver_cancers.html?qt=liver cancers&alt=sh accessed Feb. 26, 2015 (Year: 2015).*

(Continued)

*Primary Examiner* — Julie Ha
*Assistant Examiner* — Kristina M Hellman
(74) *Attorney, Agent, or Firm* — Sughrue Mion, PLLC

(57) ABSTRACT

A composition containing a glucagon derivative and a GLP-1 and GIP receptor dual agonist, and uses thereof are disclosed. The glucagon derivative comprises an amino acid sequence of the formula 1: X1-X2-QGTF-X7-SD-X10-S-X12-X13-X14-X15-X16-X17-X18-X19-X20-X21-F-X23-X24-WL-X27-X28-X29-X30 (Formula 1). The composition is useful in preventing or treating metabolic syndrome.

6 Claims, 5 Drawing Sheets

Specification includes a Sequence Listing.

(56) References Cited

OTHER PUBLICATIONS

Merck Manual, “metastatic liver cancer”, at URL www.merckmanuals.com/home/liver_and_gallbladder_disorders/tumors_of_the_liver/metastatic_liver_cancer.html accessed Feb. 26, 2015 (Year: 2015).*
Merck Manual, “overview of blood vessel disorders of the liver”, at URL merckmanuals.com/home/liver_and_gallbladder_disorders/blood_vessel_disorders_of_the_liver/overview_of_blood_vessel_disorders_of_the_liver.html accessed Feb. 26, 2015 (Year: 2015).*
Lam, Merck manual, “Atherosclerosis”, at URL merckmanuals.com/professional/cardiovascular-disorders/arteriosclerosis/atherosclerosis, accessed Dec 2015 (Year: 2015).*
Merck manual, “overview of stroke”, at URL merckmanuals.com/professional/neurologic-disorders/stroke/overview-of-stroke, accessed Nov. 2025. (Year: 2025).*
Merck manual, “hypertension”, at URL merckmanuals.com/professional/cardiovascular-disorders/hypertension/hypertension, accessed Nov. 2025 (Year: 2025).*
Lee et al, “GLP-1 based combination therapy for obesity and diabetes,” J Obes Met Synd 26:155-160 (2017) (Year: 2017).*
Communication dated Dec. 13, 2023 issued by the European Patent Office in EP application No. 20872428.6.
Marie Bastin et al., “Dual GIP-GLP1-Receptor Agonists in the Treatment of Type 2 Diabetes: A Short Review on Emerging Data and Therapeutic Potential”, Diabetes Metab Syndr, Sep. 3, 2019, 15 pgs., vol. 12.
Kira Harris et al., “Efficacy and tolerability of glucagon-like peptide-1 receptor agonists in patients with type 2 diabetes mellitus”, Therapeutic Advances in Endocrinology and Metabolism, 2015, pp. 3-18, vol. 6, No. 1.
G.J. Webb et al., “The immunogenetics of primary biliary cirrhosis: A comprehensive review”, Journal of Autoimmunity, 2015, pp. 42-52, vol. 64.
International Search Report for PCT/KR2020/013467 dated, Jan. 14, 2021 (PCT/ISA/210).

* cited by examiner

[FIG. 1]
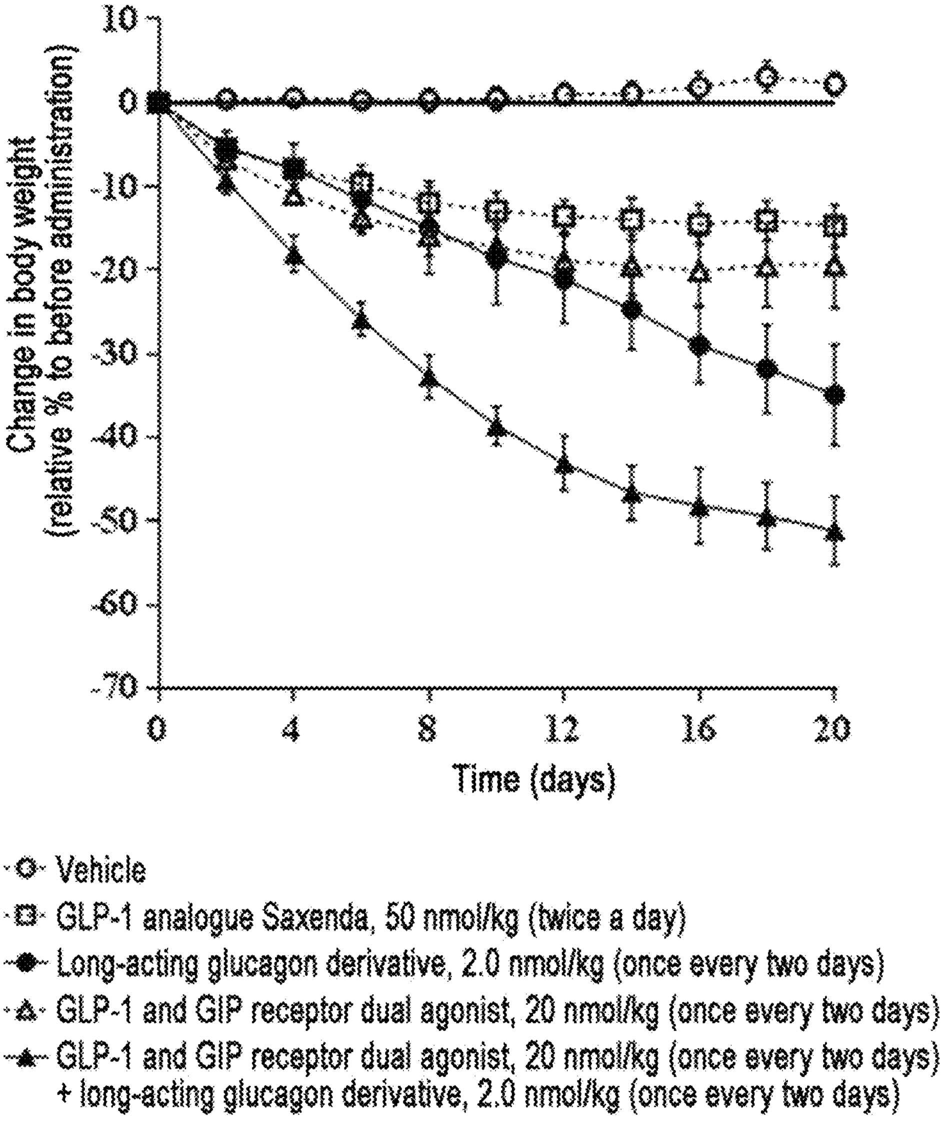

[FIG. 2(A)]
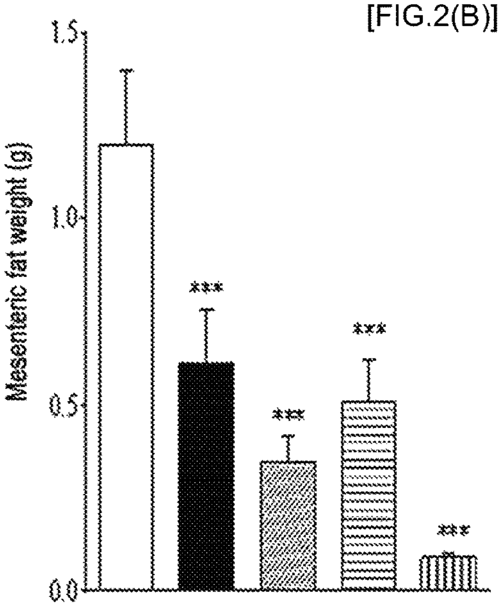
[FIG.2(B)]
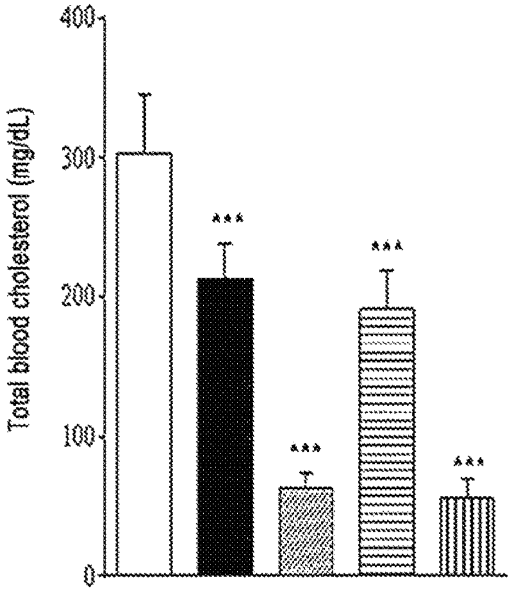
Vehicle
GLP-1 analogue Saxenda, 50 nmol/kg (twice a day)
Long-acting glucagon derivative, 2.0 nmol/kg (once every two days)
GLP-1 and GIP receptor dual agonist, 20 nmol/kg (once every two days)
GLP-1 and GIP receptor dual agonist, 20 nmol/kg (once every two days)
+ long-acting glucagon derivative, 2.0 nmol/kg (once every two days)

[FIG. 3(A)]
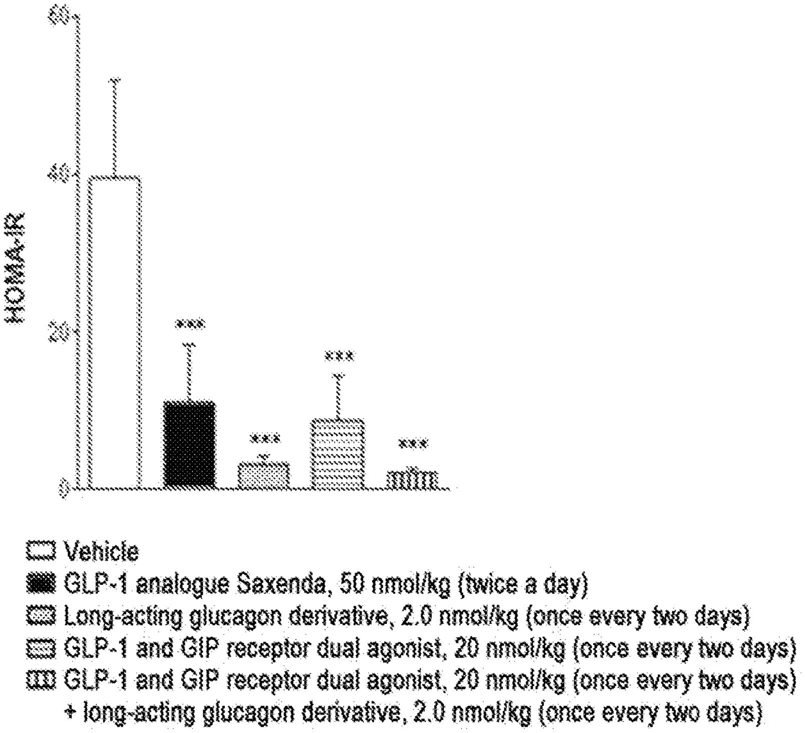
[FIG. 3(B)]
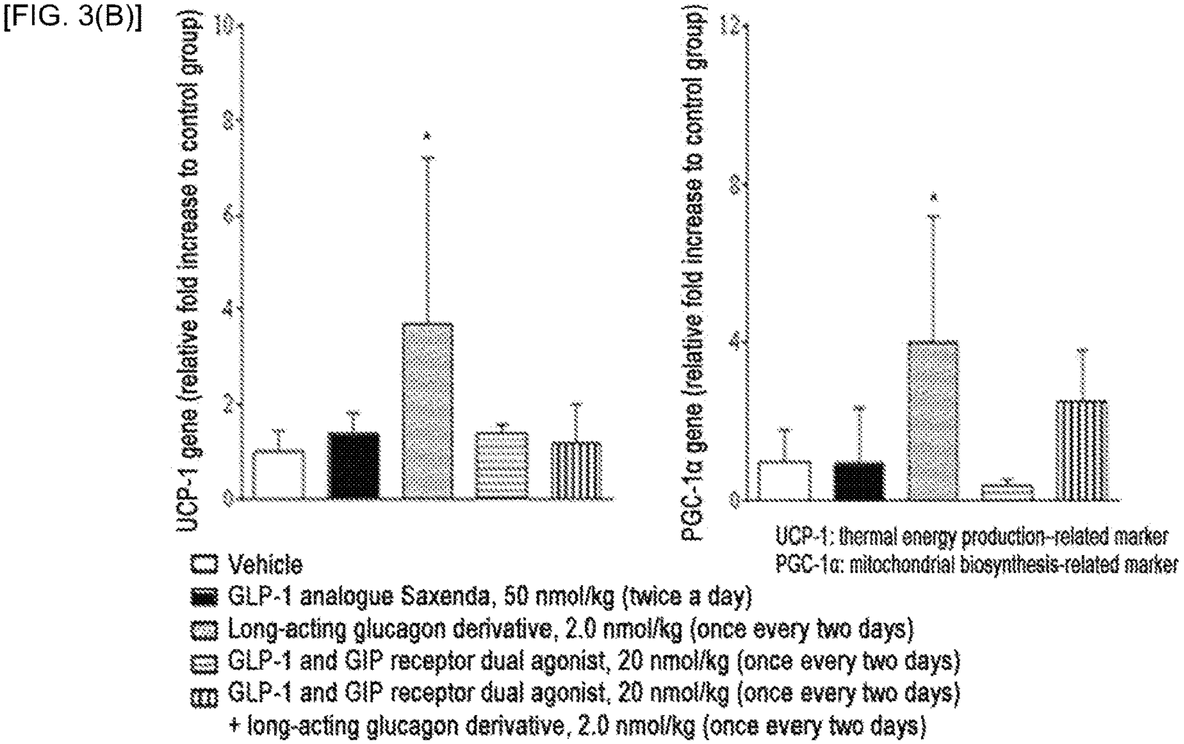

[FIG. 4]
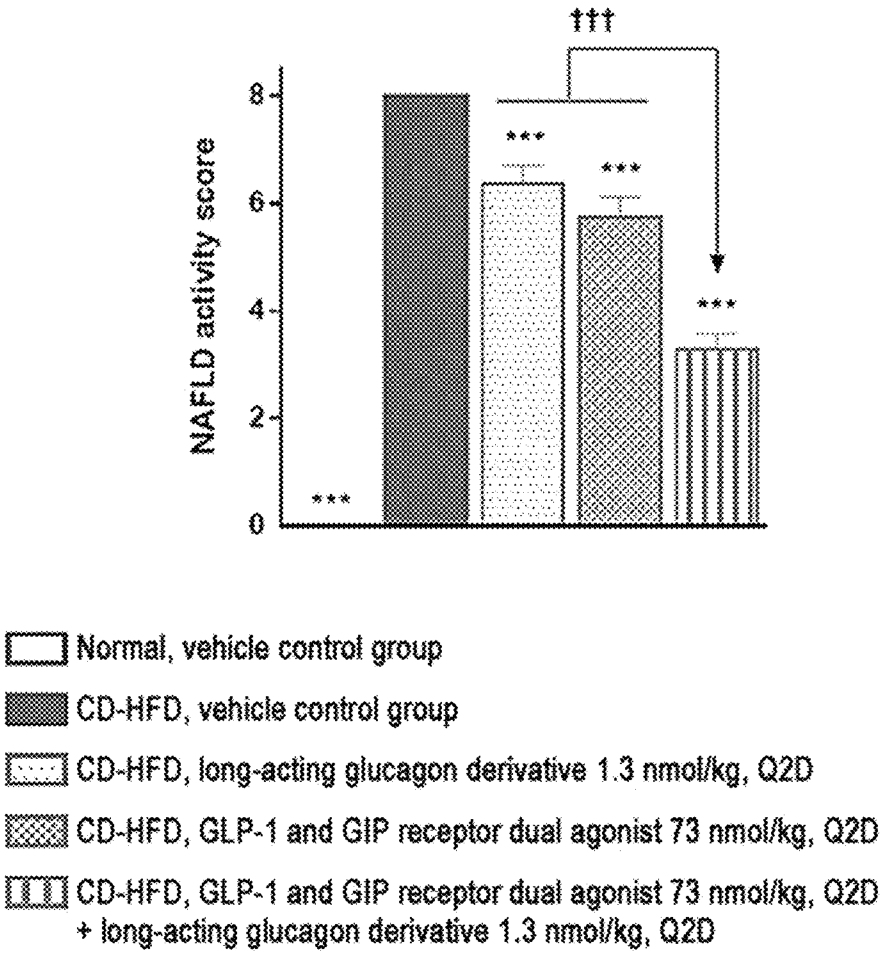

[FIG. 5]
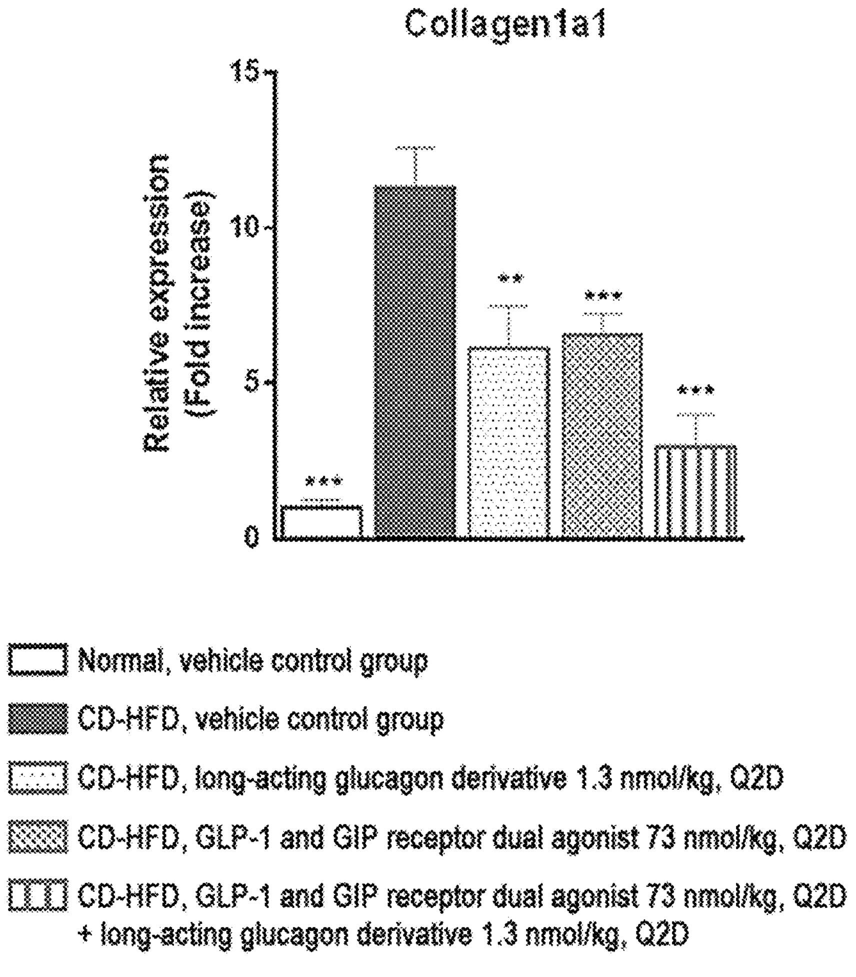

COMPOSITION COMPRISING GLUCAGON AND GLP-1 AND GIP RECEPTOR DUAL AGONIST AND THERAPEUTIC USE OF SAME

CROSS REFERENCE TO RELATED APPLICATIONS

This application is a National Stage of International Application No. PCT/KR2020/013467 filed Oct. 5, 2020, claiming priority based on Korean Patent Application No. 10-2019-0123250 filed Oct. 4, 2019.

SEQUENCE LISTING

The content of the electronically submitted sequence listing, file name: Sequence_Listing_As_Filed.txt; size: 33,802 bytes; and date of creation: Mar. 31, 2022, filed herewith, is incorporated herein by reference in its entirety.

TECHNICAL FIELD

The present invention relates to a composition comprising a compound or substance exhibiting glucagon activity and a GLP-1 and GIP receptor dual agonist, and therapeutic use of the same.

BACKGROUND ART

Recently, the incidence of metabolic syndrome-related diseases including various diseases such as obesity, hyperlipidemia, hypertension, arteriosclerosis, hyperinsulinemia, diabetes, or liver disease has rapidly increased along with economic development and changes in dietary habits. These diseases may occur individually but are usually closely related to each other and occur together with various symptoms in most cases.

Overweight and obesity increase blood pressure and cholesterol levels, which are causes of the onset or exacerbation of various diseases such as heart disease, diabetes, and arthritis. In addition, overweight and obesity are major factors that increase the incidence of arteriosclerosis, hypertension, hyperlipidemia, or heart disease in children and adolescents as well as adults.

Obesity is a complex disease involving mechanisms of action of appetite control and energy metabolism, and thus methods of treating abnormal mechanisms of action related to appetite control and energy metabolism are required to be performed simultaneously, and efforts to develop a drug capable of treating the abnormal mechanisms of action are continuously being made. As a result of the efforts, anti-obesity drugs such as rimonabant (Sanofi-Aventis), sibutramine (Abbott), contrave (Takeda), orlistat (Roche) have been developed, but these have the disadvantages of showing fatal side effects or having insufficient effects on the treatment of obesity. For example, it has been reported that rimonabant shows central nervous system side effects, sibutramine and contrave show cardiovascular side effects, and orlistat has a body weight loss effect of only about 4 kg when taken for one year.

Meanwhile, metabolic syndrome including obesity increases the likelihood of causing diseases in the liver. Examples thereof include metabolic liver disease, fatty liver, non-alcoholic fatty liver disease, steatohepatitis, and liver fibrosis. These liver diseases are increasing along with the increase in the population with obesity and diabetes, and the annual incidence rate in Korea is about 16%. Liver disease has no symptoms at the early stages and is only discovered at a fairly advanced stage, and is thus a leading cause of death not only in Korea but also worldwide, and the development of drugs for liver disease is highly required.

Meanwhile, glucagon is produced in the pancreas when blood sugar starts to drop due to causes such as drug treatment or disease, hormone or enzyme deficiency, and the like. Glucagon is responsible for signaling the liver to break down glycogen to release glucose and raising the blood sugar levels to normal levels. However, the use of glucagon as a therapeutic agent has been limited because of its low solubility and precipitation at neutral pH.

Glucagon-like peptide-1 (GLP-1), a glucagon derivative, is a hormone secreted from the small intestine when stimulated by food intake, and promotes insulin secretion from the pancreas in a blood sugar concentration-dependent manner and inhibits glucagon secretion to help lower blood sugar levels. Glucagon-like peptide-1 (GLP-1) acts as a satiety factor to slow gastrointestinal digestion and delays the gastrointestinal transit time of digested food to diminish food intake.

Together with GLP-1, GIP, one of the gastrointestinal hormones secreted when stimulation due to food intake occurs, is a hormone composed of 42 amino acids secreted from K cells in the small intestine and functions to promote insulin secretion from the pancreas in a blood sugar concentration-dependent manner and to help lower blood sugar levels. The GLP-1 activity increasing effect, anti-inflammatory effect, lipid metabolism improving effect, and the like of GIP have been reported.

Accordingly, studies to develop a therapeutic agent for diabetes and obesity by using the blood sugar control and body weight loss effects of GLP-1 are being actively conducted. However, GLP-1 alone shows HbA1c reduction of only 0.5% to 1.8%. and is thus considered to be appropriate for patients with HbA1c of 9% or less (*Ther Adv Endocrinol Metab.* 2015 February; 6(1):3-18). In other words, there is a limit to the blood sugar control ability that can be expected due to single administration of GLP-1.

Accordingly, studies on dual agonists capable of simultaneously activating GLP-1 and GIP receptors have been conducted, and examples of such dual agonists are described in WO 2013164483. WO 2016111971, WO 2014192284, and the like.

The glucagon and GLP-1 and GIP receptor dual agonists are generally known to have opposite actions, and have been used as therapeutic agents for different symptoms of disease. In other words, glucagon and GLP-1 and GIP receptor dual agonists perform opposite roles in the body, and drug treatment by concurrent administration of these has not yet been reported. Meanwhile, when various metabolic syndrome-related therapeutic agents are administered to a patient, there is a risk of side effects such as weight gain, overdose, and hypoglycemia.

DISCLOSURE

Technical Problem

An object of the present invention relates to a pharmaceutical composition for preventing or treating metabolic syndrome, which comprises a substance exhibiting activity with respect to the glucagon receptor and a GLP-1 and GIP receptor dual agonist.

Another object of the present invention is to provide a method for preventing or treating metabolic syndrome, which comprises administering a substance exhibiting activity with respect to the glucagon receptor and a GLP-1 and GIP receptor dual agonist to an individual in need thereof.

Still another object of the present invention is to provide the use of a substance exhibiting activity with respect to the glucagon receptor and a GLP-1 and GIP receptor dual agonist for the prevention or treatment of metabolic syndrome.

Technical Solution

An aspect embodying the present invention is therapeutic use of a substance exhibiting activity with respect to the glucagon receptor and a GLP-1 and GIP receptor dual agonist in combination.

In an embodiment, the present invention relates to a composition comprising a substance exhibiting activity with respect to the glucagon receptor and a GLP-1 and GIP receptor dual agonist.

In the preceding embodiment, the present invention relates to a pharmaceutical composition for preventing or treating metabolic syndrome, which comprises a substance exhibiting activity with respect to the glucagon receptor and a GLP-1 and GIP receptor dual agonist.

In the preceding embodiment(s), the substance exhibiting activity with respect to the glucagon receptor is a peptide including an amino acid sequence represented by the following Formula 1:

```
                                   (Formula 1, SEQ ID NO: 46)
X1-X2-QGTF-X7-SD-X10-S-X12-X13-X14-X15-X16-X17-
X18-X19-X20-X21-F-X23-X24-WL-X27-X28-X29-X30
```

wherein X1 is tyrosine (Y);

X2 is α-methyl-glutamic acid (α-methyl-glutamic acid), Aib (aminoisobutyric acid), D-alanine, glycine (G), Sar (N-methylglycine), serine (S), or D-serine;

X7 is threonine (T), valine (V), or cysteine (C);

X10 is tyrosine (Y) or cysteine (C);

X12 is lysine (K) or cysteine (C);

X13 is tyrosine (Y) or cysteine (C);

X14 is leucine (L) or cysteine (C);

X15 is aspartic acid (D), glutamic acid (E), or cysteine (C);

X16 is glutamic acid (E), aspartic acid (D), serine (S), α-methyl-glutamic acid, or cysteine (C) or absent;

X17 is aspartic acid (D), glutamine (Q), glutamic acid (E), lysine (K), arginine (R), serine (S), cysteine (C), or valine (V) or absent;

X18 is alanine (A), aspartic acid (D), glutamic acid (E), arginine (R), valine (V), or cysteine (C) or absent;

X19 is alanine (A), arginine (R), serine (S), valine (V), or cysteine (C) or absent;

X20 is lysine (K), histidine (H), glutamine (Q), aspartic acid (D), arginine (R), α-methyl-glutamic acid, or cysteine (C) or absent;

X21 is aspartic acid (D), glutamic acid (E), leucine (L), valine (V), or cysteine (C) or absent;

X23 is isoleucine (1), valine (V), or arginine (R) or absent;

X24 is valine (V), arginine (R), alanine (A), cysteine (C), glutamic acid (E), lysine (K), glutamine (Q), α-methyl-glutamic acid, or leucine (L) or absent;

X27 is isoleucine (1), valine (V), alanine (A), lysine (K), methionine (M), glutamine (Q), or arginine (R) or absent;

X28 is glutamine (Q), lysine (K), asparagine (N), or arginine (R) or absent;

X29 is threonine (T); and

X30 is cysteine (C) or absent (with the proviso that when the amino acid sequence represented by Formula 1 is identical to SEQ ID NO: 1 or SEQ ID NO: 12, it is excluded).

In the preceding embodiment(s), the peptide is in the form of a long-acting conjugate, and the long-acting conjugate is represented by the following Chemical Formula 1:

X-L-F [Chemical Formula 1]

wherein X is a peptide including the amino acid sequence represented by Formula 1;

L is a linker containing an ethylene glycol repeating unit;

F is an immunoglobulin Fc region; and

— represents linkage between X and L and between L and F by a covalent bond.

In the preceding embodiment(s), in Formula 1,

X2 is Aib (aminoisobutyric acid);

X7 is threonine (T), valine (V), or cysteine (C);

X10 is tyrosine (Y);

X12 is lysine (K);

X13 is tyrosine (Y);

X14 is leucine (L) or cysteine (C):

X15 is aspartic acid (D);

X16 is glutamic acid (E) or serine (S);

X17 is lysine (K), arginine (R), or cysteine (C);

X18 is arginine (R);

X19 is alanine (A) or cysteine (C);

X20 is glutamine (Q) or lysine (K);

X21 is aspartic acid (D) or glutamic acid (E);

X23 is valine (V);

X24 is glutamine (Q);

X27 is methionine (M);

X28 is asparagine (N):

X29 is threonine (T); and

X30 is cysteine (C) or absent.

In the preceding embodiment(s), the peptide includes an amino acid sequence selected from the group consisting of SEQ ID NOs: 2 to 45.

In the preceding embodiment(s), the peptide includes an amino acid sequence selected from the group consisting of SEQ ID NOs: 7 to 11, 13 to 25, 27, 29, 31, 33, and 35 to 45.

In the preceding embodiment(s), the peptide includes an amino acid sequence selected from the group consisting of SEQ ID NOs: 20, 22, 23, 27, 33, 35, 37, 38, 40, 41, 42, and 44.

In the preceding embodiment(s), each amino acid forms a ring in at least one of amino acid pairs of X10 and X14, X12 and X16, X16 and X20, X17 and X21, X20 and X24, and X24 and X28 in Formula 1.

In the preceding embodiment(s), a C-terminus of the peptide is amidated.

In the preceding embodiment(s), the GLP-1 and GIP receptor dual agonist is a substance exhibiting activity with respect to a GLP-1 (glucagon-like peptide-1) receptor and a GIP (glucose-dependent insulinotropic polypeptide) receptor.

In the preceding embodiment(s), the GLP-1 and GIP receptor dual agonist is one or more selected from the group consisting of tirzepatide, NN9709, and SAR-438335.

In the preceding embodiment(s), the chemical formula weight of an ethylene glycol repeating unit moiety in L is in a range of 1 kDa to 100 kDa.

In the preceding embodiment(s), the metabolic syndrome is selected from the group consisting of impaired glucose tolerance, hypercholesterolemia, dyslipidemia, obesity, diabetes, hypertension, liver disease, arteriosclerosis caused by dyslipidemia, atherosclerosis, arteriosclerosis, coronary artery heart disease (coronary heart disease), and stroke.

In the preceding embodiment(s), the liver disease is at least one disease selected from the group consisting of simple steatosis, non-alcoholic fatty liver, liver inflammation, non-alcoholic steatohepatitis (NASH), cholestasis liver disease, liver fibrosis, liver cirrhosis, liver decompensation, and hepatocellular carcinoma.

In the preceding embodiment(s), the cholestasis liver disease is any one selected from the group consisting of primary biliary cirrhosis, primary sclerosing cholangitis, and a combination thereof.

In the preceding embodiment(s), the liver disease is due to or accompanied by non-alcoholic steatohepatitis.

In the preceding embodiment(s), the composition performs one or more of the following properties:

(a) body weight and fat weight loss;

(b) improving blood lipid levels;

(c) improving insulin sensitivity:

(d) reducing UCP-1 and PGC-1α gene expression;

(e) reducing NAS (NAFLD activity score); and (f) reducing collagen expression in liver tissue.

Another aspect embodying the present invention is a pharmaceutical kit for preventing or treating metabolic syndrome, which comprises a substance exhibiting activity with respect to the glucagon receptor and a GLP-1 and GIP receptor dual agonist; or a composition comprising these.

Still another aspect embodying the present invention is a method for preventing or treating metabolic syndrome, which comprises administering a substance exhibiting activity with respect to the glucagon receptor and a GLP-1 and GIP receptor dual agonist; or a composition comprising these to an individual in need thereof.

Still another aspect embodying the present invention is the use of a substance exhibiting activity with respect to the glucagon receptor and a GLP-1 and GIP receptor dual agonist; or a composition comprising these for the prevention or treatment of metabolic syndrome.

Still another aspect embodying the present invention is the use of a substance exhibiting activity with respect to the glucagon receptor and a GLP-1 and GIP receptor dual agonist; or a composition comprising these for the preparation of a medicament for preventing or treating metabolic syndrome.

Advantageous Effects

The combined administration of the substance exhibiting activity with respect to the glucagon receptor and the GLP-1 and GIP receptor dual agonist according to the present invention can be usefully used for the prevention or treatment of metabolic syndrome, including obesity, diabetes, and non-alcoholic steatohepatitis (NASH), and liver diseases related thereto.

BRIEF DESCRIPTION OF DRAWINGS

FIG. 1 is a result of confirming changes in body weight by combined administration of a long-acting glucagon derivative and tirzepatide, a GLP-1 and GIP receptor dual agonist;

FIGS. 2(A) and 2(B) are results of confirming decreases in fat weight and blood lipids by combined administration of a long-acting glucagon derivative and tirzepatide, a GLP-1 and GIP receptor dual agonist, respectively;

FIGS. 3(A) and 3(B) are results of confirming increases in insulin sensitivity and UCP-1 and PGC-1a gene expression by combined administration of a long-acting glucagon derivative and tirzepatide, a GLP-1 and GIP receptor dual agonist, respectively;

FIG. 4 is a result of confirming changes in NAS (NAFLD activity score) by combined administration of a long-acting glucagon derivative and tirzepatide, a GLP-1 and GIP receptor dual agonist; and FIG. 5 is a result of confirming the reduction in collagen expression in liver tissue by combined administration of a long-acting glucagon derivative and tirzepatide, a GLP-1 and GIP receptor dual agonist.

DETAILED DESCRIPTION OF THE INVENTION

Specific details for carrying out the present invention will be described as follows. Each description and embodiment disclosed in this disclosure may also be applied to other descriptions and embodiments. That is, all combinations of various elements disclosed in this disclosure fall within the scope of the present invention. Further, the scope of the present invention is not limited by the specific description below.

Further, those skilled in the art will recognize, or be able to ascertain using no more than routine experimentation, many equivalents to the specific aspects of the present invention described herein. Further, these equivalents should be interpreted to fall within the scope of the present invention.

Throughout this specification, not only ordinary one-letter and three-letter codes for naturally occurring amino acids but also commonly accepted three-letter codes for other amino acids such as Aib (α-aminoisobutyric acid) and Sar (N-methylglycine) are used. Amino acids referred to by abbreviation herein are also described according to the IUPAC-IUB nomenclature.

Alanine A Arginine R
Asparagine N Aspartic acid D
Cysteine C Glutamic acid E
Glutamine Q Glycine G
Histidine H Isoleucine I
Leucine L Lysine K
Methionine M Phenylalanine F
Proline P Serine S
Threonine T Tryptophan W
Tyrosine Y Valine V An aspect embodying the present invention provides therapeutic use of a substance exhibiting activity with respect to the glucagon receptor and a GLP-1 and GIP receptor dual agonist in combination.

Specifically, an aspect of the present invention provides a composition comprising a substance exhibiting activity with respect to the glucagon receptor; and a GLP-1 and GIP receptor dual agonist. In an embodiment, a pharmaceutical composition for preventing or treating metabolic syndrome is provided.

The pharmaceutical composition comprising (i) a substance exhibiting activity with respect to the glucagon receptor; and (ii) a GLP-1 and GIP receptor dual agonist of the present invention may be in a form a) in which (i) the substance exhibiting activity with respect to the glucagon receptor; and (ii) the GLP-1 and GIP receptor dual agonist may be administered as a mixture; or a form b) in which (i) the substance exhibiting activity with respect to the glucagon receptor; and (ii) the GLP-1 and GIP receptor dual agonist can be administered may be administered in separate forms, but is not limited thereto.

For example, the substance exhibiting activity with respect to the glucagon receptor and the GLP-1 and GIP receptor dual agonist may be formulated as one preparation, or separately formulated. When the substance exhibiting activity with respect to the glucagon receptor; and the GLP-1 and GIP receptor dual agonist are in separate forms, the substance exhibiting activity with respect to the glucagon receptor and the GLP-1 and GIP receptor dual agonist may be formulated as separate preparations and administered simultaneously, separately, sequentially, or in reverse order.

In the present invention, combined administration means not only simultaneous administration but is also understood as a dosage form in which the substance exhibiting activity with respect to the glucagon receptor and the GLP-1 and GIP receptor dual agonist act together on an individual so that each of these may perform a function at a level equal to or higher than its intended function. Accordingly, as used herein, the term "combined administration" is to be understood as referring to the simultaneous, separate, sequential, or reverse administration of the substance exhibiting activity with respect to the glucagon receptor and the GLP-1 and GIP receptor dual agonist. When the administration is sequential, reversed or separate administration, the order of administration is not particularly limited, but the administration interval of the second component is required to be such that the beneficial effect of the combined administration is not lost.

The substance exhibiting activity with respect to the glucagon receptor and the GLP-1 and GIP receptor dual agonist, or a composition comprising these of the present invention may be provided in the form of a kit, but is not limited thereto. As used herein, the term "kit" may include the composition according to the present invention for combined administration of the substance exhibiting activity with respect to the glucagon receptor and the GLP-1 and GIP receptor dual agonist. Specifically, the kit according to the present invention may comprise the substance exhibiting activity with respect to the glucagon receptor and the GLP-1 and GIP receptor dual agonist formulated as one preparation, or separate preparations of the substance exhibiting activity with respect to the glucagon receptor and the GLP-1 and GIP receptor dual agonist, and may additionally comprise a substance necessary for combined administration of the two substances, but is not limited thereto.

The substance exhibiting activity with respect to the glucagon receptor includes various substances exhibiting a significant level of activity with respect to the glucagon receptor, for example, substances in the form of compounds or peptides.

Although not particularly limited thereto, the substance exhibiting a significant level of activity with respect to the glucagon receptor is not only native glucagon, but may also be one that exhibits in vitro activity with respect to the glucagon receptor to be 0.1% or more, 1% or more, 2% or more, 3% or more, 4% or more, 5% or more, 6% or more, 7% or more, 8% or more, 9% or more, 10% or more, 20% or more, 30% or more or more, 40% or more, 50% or more, 60% or more, 70% or more, 80% or more, 90% or more, or 100% or more of that of a native ligand (native glucagon) of the corresponding receptor.

Examples of the substance exhibiting activity with respect to the glucagon receptor include native glucagon, an agonist thereof, or a derivative thereof, but are not particularly limited thereto.

The glucagon derivative according to the present invention includes peptides having one or more differences in amino acid sequence compared to native glucagon, peptides in which the native glucagon sequence is modified through modification, native glucagon mimics capable of activating the glucagon receptor like native glucagon. For example, the derivative of native glucagon is one in which one or more amino acids are mutated from the native glucagon, and the mutation may be a mutation selected from the group consisting of substitution, addition, deletion, modification, and any combination thereof, but is not particularly limited thereto.

Such a glucagon derivative may have a changed pI with respect to native glucagon to exhibit improved physical properties. The glucagon derivative may exhibit improved solubility while retaining the activity of activating the glucagon receptor, but is not limited thereto.

The glucagon derivative may be glucagon derivatives which do not occur naturally.

Native glucagon may have the following amino acid sequence:

```
                                         (SEQ ID NO: 1)
His-Sre-Gln-Gly-Thr-Phe-Thr-Ser-Asp-Tyr-Ser-Lys-
Tyr-Leu-Asp-Ser-Arg-Arg-Ala-Gln-Asp-Phe-Val-Gln-
Trp-Leu-Met-Asn-Thr.
```

As used herein, the term "isoelectric point" or "pI" refers to a pH value at which there is no net charge (0) in a certain molecule such as a polypeptide or peptide. For polypeptides in which various charged functional groups are present, the sum of these charges at pI is zero. The overall net charge of polypeptide will be negative at a pH higher than pI, and the overall net charge of polypeptide will be positive at a pH value lower than pI.

The pI may be determined by isoelectric point electrophoresis on a fixed pH gradient gel composed of polyacrylamide, starch or agarose, or by, for example, estimating the pI from the amino acid sequence using the pI/MW tool (expasy.org/tools/pi_tool.html; Gasteiger et al., 2003) on the ExPASy server.

As used herein, the term "changed pI" means that some sequences in the amino acid sequence of native glucagon are substituted with negatively and positively charged amino acid residues to have a pI different from that of native glucagon, namely, a pI decreased or increased from that of native glucagon. Peptides having this changed pI may exhibit improved solubility and/or high stability at neutral pH as glucagon derivatives. However, the peptide is not particularly limited thereto.

More specifically, the glucagon derivative may have a changed pI value rather than the pI value (6.8) of native glucagon, still more specifically a pI value of less than 6.8, specifically 6.7 or less, more specifically 6.5 or less, and a pI value of specifically more than 6.8, 7 or more, more specifically 7.5 or more, but is not limited thereto. A glucagon derivative is included in the scope of the present invention as long as it has a pI value different from that of native glucagon. In particular, a glucagon derivative is particularly included in the scope of the present invention as long as it has a pI value different from that of native glucagon, thus exhibits improved solubility compared to the native glucagon at neutral pH, and as a result, the degree of aggregation thereof is low.

More specifically. the glucagon derivative may have a pI value of 4 to 6.5 and/or 7 to 9.5, more specifically 7.5 to 9.5, still more specifically 8.0 to 9.3, but is not limited thereto. In this case, the glucagon derivative has a pI higher or lower than that of native glucagon, and may thus exhibit improved solubility and higher stability compared to native glucagon at neutral pH. However, the glucagon derivative is not limited thereto.

Specifically, derivatives of native glucagon may be modified through any one method of substitution, addition, deletion or modification of some amino acids in native glucagon or any combination of these methods.

Examples of glucagon derivatives prepared by a combination of these methods include peptides having one or more amino acid sequences different from those of native glucagon, deamination at the N-terminal amino acid residue, and a function of activating the glucagon receptor, but are not limited thereto. A derivative of native glucagon applied to the present invention may be prepared by combining various methods for preparing derivatives.

Such modifications for the preparation of derivatives of native glucagon include all of modifications using L-amino acids or D-amino acids, and/or non-natural amino acids; and/or modifications of the native sequence, for example, modification of side chain functional groups and modifications of intramolecular covalent bonds such as inter-chain ring formation, methylation, acylation, ubiquitination, phosphorylation, aminohexylation, and biotinylation. The modifications include all of substitutions with non-natural compounds.

The modifications include all those in which one or more amino acids are added to the amino and/or carboxy terminus of native glucagon.

As the amino acids to be substituted or added, not only the 20 amino acids commonly found in human proteins but also atypical amino acids or those that do not occur naturally may be used. Commercial sources of atypical amino acids include Sigma-Aldrich, ChemPep and Genzyme Pharmaceuticals. Peptides including these amino acids and canonical peptide sequences may be synthesized by and purchased from commercial peptide synthesis companies, for example, American peptide company or Bachem in the United States or Anygen in Korea.

Amino acid derivatives may also be procured in the same way, and to name just a few examples, 4-imidazoacetic acid and the like may be used.

Glucagon has a pI of about 7, thus is insoluble in solutions at physiological pH (pH 4 to 8), and tends to precipitate at neutral pH. In an aqueous solution of pH 3 or lower, glucagon is initially dissolved but precipitates within 1 hour due to gel formation. The gelled glucagon mainly consists of β-sheet fibrils, and the glucagon thus precipitated is not suitable for use as an injection since the gel clogs blood vessels when administered intravenously or by needle. In order to delay the precipitation process, it is customary to use an acidic (pH 2 to 4) formulation, and this can keep glucagon in a relatively non-aggregated state for a short period of time. However, since the fibril formation of glucagon occurs remarkably rapidly at low pH, such an acidic formulation is required to be injected immediately after preparation.

The substance exhibiting activity with respect to the glucagon receptor of the present invention is a glucagon derivative, and includes those developed to have an extended action profile by changing the pI of native glucagon through substitution of negatively and positively charged amino acid residues. These derivatives have a changed pI compared to native glucagon at neutral pH and may thus exhibit improved solubility and/or higher stability.

As a specific aspect, the glucagon derivative, which is the substance exhibiting activity with respect to the glucagon receptor of the present invention, may be a peptide including an amino acid sequence represented by the following Formula 1.

```
                                (Formula 1, SEQ ID NO: 46)
X1-X2-QGTF-X7-SD-X10-S-X12-X13-X14-X15-X16-X17-
X18-X19-X20-X21-F-X23-X24-WL-X27-X28-X29-X30
```

In Formula 1,

X1 may be tyrosine;

X2 may be α-methyl-glutamic acid, Aib (aminoisobutyric acid), D-alanine, glycine, Sar (N-methylglycine), serine, or D-serine;

X7 may be threonine, valine, or cysteine;

X10 may be tyrosine or cysteine;

X12 may be lysine or cysteine;

X13 may be tyrosine or cysteine;

X14 may be leucine or cysteine;

X15 may be aspartic acid, glutamic acid, or cysteine;

X16 may be glutamic acid, aspartic acid, serine, α-methyl-glutamic acid, or cysteine or absent;

X17 may be aspartic acid, glutamine, glutamic acid, lysine, arginine, serine, cysteine, or valine or absent;

X18 may be alanine, aspartic acid, glutamic acid, arginine, valine, or cysteine or absent;

X19 may be alanine, arginine, serine, valine, or cysteine or absent;

X20 may be lysine, histidine, glutamine, aspartic acid, arginine, α-methyl-glutamic acid, or cysteine or absent;

X21 may be aspartic acid, glutamic acid, leucine, valine, or cysteine or absent;

X23 may be isoleucine, valine, or arginine or absent;

X24 may be valine, arginine, alanine, cysteine, glutamic acid, lysine, glutamine, α-methyl-glutamic acid, or leucine or absent;

X27 may be isoleucine, valine, alanine, lysine, methionine, glutamine, or arginine or absent;

X28 may be glutamine, lysine, asparagine, or arginine or absent;

X29 may be threonine; and

X30 may be cysteine or absent (with the proviso that when the amino acid sequence represented by Formula 1 is identical to SEQ ID NO: 1 or SEQ ID NO: 12, it is excluded).

In Formula 1,

X1 may be tyrosine;

X2 may be serine or Aib (aminoisobutyric acid);

X7 may be threonine, valine, or cysteine;

X10 may be tyrosine or cysteine;

X12 may be lysine or cysteine;

X13 may be tyrosine or cysteine;

X14 may be leucine or cysteine;

X15 may be aspartic acid or cysteine;

X16 may be glutamic acid, serine, or cysteine;

X17 may be aspartic acid, glutamic acid, lysine, arginine, serine, cysteine, or valine:

X18 may be aspartic acid, glutamic acid, arginine, or cysteine;

X19 may be alanine or cysteine;

X20 may be glutamine, aspartic acid, lysine, or cysteine;

X21 may be aspartic acid, glutamic acid, leucine, valine, or cysteine;

X23 may be isoleucine, valine, or arginine;

X24 may be valine, arginine, alanine, glutamic acid, lysine, glutamine, or leucine;

X27 may be isoleucine, valine, alanine, methionine, glutamine, or arginine:

X28 may be glutamine, lysine, asparagine, or arginine;

X29 may be threonine; and

X30 may be cysteine or absent, but the glucagon derivative is not limited thereto (with the proviso that when the amino acid sequence represented by Formula 1 is identical to SEQ ID NO: 1 or SEQ ID NO: 12, it is excluded).

For example, the peptide may include an amino acid sequence selected from the group consisting of SEQ ID NOs: 7 to 11, 13 to 25, 27, 29, 31, 33, and 35 to 45, and specifically may (essentially) consist of an amino acid sequence selected from the group consisting of SEQ ID NOs: 7 to 11, 13 to 25, 27, 29, 31, 33, and 35 to 45, but is not limited thereto.

In Formula 1,

X2 may be Aib (aminoisobutyric acid);

X7 may be threonine (T), valine (V), or cysteine (C):

X10 may be tyrosine (Y);

X12 may be lysine (K);

X13 may be tyrosine (Y);

X14 may be leucine (L) or cysteine (C);

X15 may be aspartic acid (D);

X16 may be glutamic acid (E) or serine (S);

X17 may be lysine (K), arginine (R), or cysteine (C);

X18 may be arginine (R);

X19 may be alanine (A) or cysteine (C);

X20 may be glutamine (Q) or lysine (K);

X21 may be aspartic acid (D) or glutamic acid (E);

X23 may be valine (V):

X24 may be glutamine (Q);

X27 may be methionine (M);

X28 may be asparagine (N);

X29 may be threonine (T); and

X30 may be cysteine (C) or absent, but the glucagon derivative is not limited thereto.

For example, the peptide may include an amino acid sequence selected from the group consisting of SEQ ID NOs: 20, 22, 23, 27, 33, 35, 37, 38, 40, 41, 42, and 44, and specifically may (essentially) consist of an amino acid sequence selected from the group consisting of SEQ ID NOs: 20, 22, 23, 27, 33, 35, 37, 38, 40, 41, 42, and 44, but is not limited thereto.

Specifically, the peptide may include an amino acid sequence selected from the group consisting of SEQ ID NOs: 20, 22, 23, 27, 33, 37, 38, and 44, and specifically may (essentially) consist of an amino acid sequence selected from the group consisting of SEQ ID NOs: 20, 22, 23, 27, 33, 37, 38, and 44, but is not limited thereto.

In Formula 1,

X1 may be tyrosine:

X2 may be serine or Aib (aminoisobutyric acid);

X7 may be cysteine, threonine, or valine;

X10 may be tyrosine or cysteine;

X12 may be lysine or cysteine;

X13 may be tyrosine or cysteine;

X14 may be leucine or cysteine:

X15 may be aspartic acid or cysteine;

X16 may be glutamic acid, serine, or cysteine;

X17 may be glutamic acid, lysine, arginine, cysteine, or valine;

X18 may be arginine or cysteine;

X19 may be alanine or cysteine;

X20 may be glutamine or lysine;

X21 may be aspartic acid, glutamic acid, valine, or cysteine:

X23 may be valine;

X24 may be valine or glutamine;

X27 may be methionine;

X28 may be asparagine or arginine;

X29 may be threonine; and

X30 may be cysteine or absent, but the glucagon derivative is not limited thereto.

For example, the peptide may include an amino acid sequence selected from the group consisting of SEQ ID NOs: 11, 13 to 17, 19 to 27, 29, 31, 33, and 35 to 45, and specifically may (essentially) consist of an amino acid sequence selected from the group consisting of SEQ ID NOs: 11, 13 to 17, 19 to 27, 29, 31, 33, and 35 to 45, but is not limited thereto.

In Formula 1,

X1 may be tyrosine;

X2 may be Aib (aminoisobutyric acid);

X7 may be cysteine, threonine, or valine;

X10 may be tyrosine or cysteine;

X12 may be lysine;

X13 may be tyrosine or cysteine;

X14 may be leucine or cysteine:

X15 may be aspartic acid or cysteine;

X16 may be glutamic acid, serine, or cysteine;

X17 may be lysine, arginine, cysteine, or valine;

X18 may be arginine or cysteine;

X19 may be alanine or cysteine;

X20 may be glutamine or lysine;

X21 may be aspartic acid, glutamic acid, or cysteine:

X23 may be valine:

X24 may be glutamine;

X27 may be methionine:

X28 may be asparagine or arginine;

X29 may be threonine; and

X30 may be cysteine or absent, but the glucagon derivative is not limited thereto.

For example, the peptide may include an amino acid sequence selected from the group consisting of SEQ ID NOs: 11, 14, 17, 19 to 25, 27, 29, 31, 33, and 35 to 44, and specifically may (essentially) consist of an amino acid sequence selected from the group consisting of SEQ ID NOs: 11, 14, 17, 19 to 25, 27, 29, 31, 33, and 35 to 44, but is not limited thereto.

In Formula 1,

X1 may be tyrosine:

X2 may be serine or Aib (aminoisobutyric acid);

X7 may be threonine, valine, or cysteine;

X10 may be tyrosine or cysteine;

X12 may be lysine or cysteine;

X13 may be tyrosine or cysteine;

X14 may be leucine or cysteine;

X15 may be aspartic acid or cysteine;

X16 may be glutamic acid, serine, or cysteine:

X17 may be aspartic acid, glutamic acid, lysine, arginine, serine, cysteine, or valine:

X18 may be aspartic acid, glutamic acid, arginine, or cysteine;

X19 may be alanine or cysteine;

X20 may be glutamine, aspartic acid, or lysine;

X21 may be aspartic acid or glutamic acid:

X23 may be valine;

X24 may be valine or glutamine;

X27 may be isoleucine or methionine:

X28 may be asparagine or arginine;

X29 may be threonine; and

X30 may be cysteine or absent, but the glucagon derivative is not limited thereto.

For example, the peptide may include an amino acid sequence selected from the group consisting of SEQ ID NOs: 7 to 11, 13 to 15, 17, 19 to 24, 27, 29, 31, 33, and 35 to 45, and specifically may (essentially) consist of an amino acid sequence selected from the group consisting of SEQ ID NOs: 7 to 11, 13 to 15, 17, 19 to 24, 27, 29, 31, 33, and 35 to 45, but is not limited thereto.

In Formula 1,

X1 may be tyrosine;

X2 may be Aib (aminoisobutyric acid);

X7 may be threonine:

X10 may be tyrosine;

X12 may be lysine;

X13 may be tyrosine;

X14 may be leucine;

X15 may be aspartic acid or cysteine;

X16 may be glutamic acid, serine, or cysteine;

X17 may be lysine or arginine:

X18 may be arginine;

X19 may be alanine;

X20 may be glutamine, cysteine, or lysine;

X21 may be aspartic acid, cysteine, valine, or glutamic acid:

X23 may be valine or arginine:

X24 may be glutamine or leucine;

X27 may be methionine:

X28 may be asparagine or arginine;

X29 may be threonine; and

X30 may be absent, but the glucagon derivative is not limited thereto.

For example, the peptide may include an amino acid sequence selected from the group consisting of SEQ ID NOs: 14, 16, 18, 19, 25, 31, 33, 37, and 44, and specifically may (essentially) consist of an amino acid sequence selected from the group consisting of SEQ ID NOs: 14, 16, 18, 19, 25, 31, 33, 37, and 44, but is not limited thereto.

More specifically, the peptide may be a peptide including an amino acid sequence represented by the following Formula 2:

```
                              (Formula 2, SEQ ID NO: 47)
Y-Aib-QGTF-X7-SD-X10-S-X12-Y-L-X15-X16-X17-R-A-
X20-X21-F-V-X24-W-L-M-N-T-X30
```

in Formula 2.

X7 may be threonine, valine, or cysteine;

X10 may be tyrosine or cysteine;

X12 may be lysine or cysteine;

X15 may be aspartic acid or cysteine;

X16 may be glutamic acid or serine;

X17 may be lysine or arginine;

X20 may be glutamine or lysine;

X21 may be aspartic acid or glutamic acid;

X24 may be valine or glutamine; and

X30 may be cysteine or absent.

For example, the peptide may include an amino acid sequence selected from the group consisting of SEQ ID NOs: 13, 15 and 36 to 45, and specifically may (essentially) consist of an amino acid sequence selected from the group consisting of SEQ ID NOs: 13, 15 and 36 to 45, but is not limited thereto. Still more specifically, the peptide includes an amino acid sequence of SEQ ID NO: 20 or 37, or is (essentially) composed of the corresponding amino acid sequence. However, the peptide is not limited thereto.

Specifically, in Formula 2.

X7 may be threonine, valine, or cysteine;

X10 may be tyrosine or cysteine;

X12 may be lysine;

X15 may be aspartic acid;

X16 may be glutamic acid or serine:

X17 may be lysine or arginine;

X20 may be glutamine or lysine;

X21 may be aspartic acid or glutamic acid;

X24 may be glutamine; and

X30 may be cysteine or absent, but the peptide is not particularly limited thereto.

For example, the peptide may include an amino acid sequence selected from the group consisting of SEQ ID NOs: 36 to 38, 40 to 42, 44, and 45, and specifically may (essentially) consist of an amino acid sequence selected from the group consisting of SEQ ID NOs: 36 to 38, 40 to 42, 44, and 45, but is not limited thereto.

As another example of the peptide, the peptide may be a peptide including an amino acid sequence selected from the group consisting of SEQ ID NOs: 2 to 11 and 13 to 45, and may specifically (essentially) consist of an amino acid sequence selected from the group consisting of SEQ ID NOs: 2 to 11 and 13 to 45, but is not limited thereto.

However, the peptides may exist in combinations excluded from the above categories, but are not particularly limited thereto, and all peptides described in the claims are included in the scope of the present invention unless otherwise stated in the claims.

In addition, even if it is described herein as a "peptide consisting of a specific SEQ ID NO", the peptide does not exclude the addition of meaningless sequences before or after the amino acid sequence of the corresponding SEQ ID NO or mutations that may occur naturally or silent mutations thereof when activity the same as or corresponding to that of the peptide composed of an amino acid sequence of the corresponding SEQ ID NO, and it is apparent that the peptide falls within the scope of the present application when having such sequence additions or mutations as well.

The contents described above may be applied to other embodiments or other aspects of the present invention, but the present invention is not limited thereto.

In the present invention, the peptide may have at least 60% or more, 65% or more, 70% or more, 75% or more, 80% or more, 85% or more, 90% or more, 91% or more, 92% or more, 93% or more, 94% or more, or 95% or more sequence identity with native glucagon, but the sequence identity is not particularly limited thereto, and may be easily determined by those skilled in the art through sequence comparison between the peptide and native glucagon.

As used herein, the term "homology" refers to a degree of similarity to the amino acid sequence of a wild type protein or a nucleotide sequence encoding the same, and includes sequences having the same sequence as the amino acid sequence or nucleotide sequence of the present invention by the above percentage or more. Such homology may also be determined by visually comparing two sequences, but may be determined using a bioinformatic algorithm that analyzes the degree of homology by aligning sequences to be compared side by side. The homology between the two amino acid sequences may be expressed as a percentage. Useful automated algorithms are available in the GAP, BESTFIT, FASTA, and TFASTA computer software modules of the Wisconsin Genetics Software Package (Genetics Computer Group, Madison, Wis., USA). Automated alignment algorithms in the modules include Needleman & Wunsch and Pearson & Lipman and Smith & Waterman alignment algorithms. Algorithms and homology determinations for other useful sequences are automated in software including FASTP, BLAST, BLAST2, PSIBLAST, and CLUSTAL W.

In the present invention, the peptide may be a peptide or a glucagon derivative exhibiting activity with respect to the glucagon receptor, but is not limited thereto.

Although not particularly limited thereto, the peptide exhibiting a significant level of activity with respect to the glucagon receptor may exhibit in vitro activity with respect to the glucagon receptor to be about 0.001% or more, about 0.01% or more, about 0.1% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, or about 100% or more of that of a native ligand (native glucagon), but ranges in which significant activity is exhibited are included without limitation. As the method for measuring such in vitro activity of peptides, reference may be made to Example 4 of the present specification, but the method is not particularly limited thereto.

As used herein, the term "about" is a range including all of ±0.5, ±0.4, ±0.3. ±0.2, ±0.1, and the like, and includes all numbers in a range equivalent to or similar to the number following the term about, but is not limited thereto.

Although not particularly limited thereto, the peptide may be peptides which do not occur naturally.

The above-described glucagon derivative may include an intramolecular bridge (for example, covalent bridge or non-covalent bridge), and may specifically be in a form including a ring. For example, the glucagon derivative may be in a form in which a ring is formed between amino acids 16 and 20 of the glucagon derivative, but is not particularly limited thereto.

Non-limiting examples of the ring may include a lactam bridge (or lactam ring).

The glucagon derivative includes all those modified to include an amino acid capable of forming a ring at a target position so as to include a ring.

Such a ring may be formed between amino acid side chains in the glucagon derivative, and may be, for example, a form in which a lactam ring is formed between a side chain of lysine and a side chain of glutamic acid, but is not particularly limited thereto.

For example, the peptide including the amino acid sequence represented by Formula 1 or Formula 2 may be one in which the amino acids of each amino acid pair of the amino acid pairs of X10 and X14, X12 and X16, X16 and X20, X17 and X21, X20 and X24, and X24 and X28 in Formula 1 or Formula 2 are each substituted with glutamic acid or lysine, but is not limited thereto. In Xn (n is a natural number), n represents the amino acid position from the N-terminus of the presented amino acid sequence.

The peptide including the amino acid sequence represented by Formula 1 or Formula 2 may be one in which each of the amino acids of the amino acid pair of X12 and X16, the amino acid pair of X16 and X20, or the amino acid pair of X17 and X21 is substituted with glutamic acid or lysine capable of forming a ring, but is not limited thereto.

The peptide may be one in which a ring (for example, a lactam ring) is formed between the respective amino acids of each amino acid pair in at least one amino acid pair among the amino acid pairs of X10 and X14, X12 and X16, X16 and X20, X17 and X21, X20 and X24, and X24 and X28 in Formula 1 or 2, but is not limited thereto.

The peptide may be one in which X16 is glutamic acid, X20 is lysine, and the side chains of X16 and X20 form a lactam ring in Formula 1 or 2, but is not limited thereto.

The peptide according to the present invention may have an unmodified N-terminus and/or C-terminus, but a modified form in which N-terminus, C-terminus and/or the like is chemically modified or protected by an organic group or amino acids are added to the peptide terminus and the like in order to protect the peptide from proteolytic enzymes in vivo and to enhance the stability is also included in the scope of the peptide according to the present invention. When the C-terminus is not modified, the terminus of the peptide according to the present invention has a carboxyl group, but is not particularly limited thereto.

In particular, in the case of chemically synthesized peptides, since the N-terminus and C-terminus are charged, the N-terminus may be acetylated and/or the C-terminus may be amidated in order to remove the charges, but the N-terminus and C-terminus are not particularly limited thereto.

Unless otherwise indicated in the present specification, the detailed description of the specification or the description of the claims on the "peptide" or the "conjugate" in which the peptide is covalently linked to a biocompatible substance according to the present invention applies not only to the corresponding peptide or conjugate but also to the scope including all forms of salts of the corresponding peptide or conjugate (for example, a pharmaceutically acceptable salt of the peptide) or solvates thereof. Accordingly, even if only a "peptide" or "conjugate" is described in the specification, the description also applies to a specific salt thereof, a specific solvate thereof, and a specific solvate of the specific salt. Such a salt form may be, for example, a form in which any pharmaceutically acceptable salt is used. The kind of the salt is not particularly limited. However, the salt is preferably in a form that is safe and effective for an individual, for example, a mammal, but is not particularly limited thereto.

The term, "pharmaceutically acceptable" refers to a substance that can be effectively used for a desired purpose without causing excessive toxicity, irritation, allergic reaction or the like within the scope of medical judgment.

As used herein, the term "pharmaceutically acceptable salt" includes salts derived from pharmaceutically acceptable inorganic acids, organic acids, or bases. Examples of suitable acids include hydrochloric acid, hydrobromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, and benzenesulfonic acid. Salts derived from suitable bases may include salts of alkali metals such as sodium and potassium, salts of alkaline earth metals such as magnesium, ammonium salts, and the like.

As used herein, the term "solvate" refers to one in which the peptide or conjugate according to the present invention or salt thereof forms a complex with a solvent molecule.

The glucagon derivative peptide of the present invention may be synthesized by way of a method well known in the art, for example, using an automatic peptide synthesizer according to its length, or may also be produced by genetic engineering techniques.

Specifically, the glucagon derivative peptide of the present invention may be prepared by standard synthetic methods, recombinant expression systems, or any other method in the art. Accordingly, the glucagon derivative according to the present invention may be synthesized by a number of methods including, for example, the following methods:

(a) a method in which a peptide is synthesized stepwise or by fragment assembly by means of a solid or liquid phase method and the final peptide product is isolated and purified; or (b) a method in which a nucleic acid construct encoding a peptide is expressed in a host cell and the expressed product is recovered from the host cell culture; or (c) cell-free in vitro expression of a nucleic acid construct encoding a peptide is performed and the expressed product is recovered; or a method in which a fragment of a peptide is obtained by any combination of (a), (b), and (c), then the fragments are ligated to obtain a peptide, and the peptide is recovered.

As a more specific example, a fusion gene encoding a fusion protein including a fusion partner and a glucagon derivative is prepared through genetic manipulation, transformed into a host cell, and then expressed in the form of fusion protein, and the glucagon derivative is cleaved and isolated from the fusion protein using a proteolytic enzyme or a compound, whereby a desired glucagon derivative may be produced. To this end, for example, a DNA sequence encoding an amino acid residue capable of being cleaved by a proteolytic enzyme such as Factor Xa or enterokinase, CNBr, or a compound such as hydroxylamine may be inserted between the fusion partner and the polynucleotide encoding the glucagon derivative.

As a more specific aspect, the peptide or glucagon derivative according to the present invention, for example, a peptide including the amino acid sequence represented by Formula 1 may be in the form of a long-acting conjugate bound to a biocompatible substance moiety that increases the in vivo half-life thereof, but is not limited thereto. The biocompatible substance moiety may be used interchangeably with a carrier.

Specifically, the conjugate includes a peptide moiety and a biocompatible substance moiety covalently linked to the peptide moiety, and the peptide moiety may be the same sequence as the amino acid sequence represented by Formula 1 or a sequence including the same.

In the present invention, the conjugate of the peptide may exhibit increased persistence of efficacy compared to a peptide to which a carrier is not bound. In the present invention, such a conjugate is referred to as a "long-acting conjugate".

Such a conjugate may be a conjugate which does not occur naturally.

As used herein, the term "long-acting conjugate" refers to a conjugate which is in a form in which a biocompatible substance moiety or carrier is bound to a physiologically active substance (for example, a glucagon derivative), and exhibits increased persistence of efficacy (for example, increased half-life in the body) compared to a physiologically active substance to which the biocompatible substance moiety or carrier is not bound. In the long-acting conjugate, the biocompatible substance moiety or carrier may be covalently linked to a physiologically active substance, but is not particularly limited thereto.

In a specific embodiment of the present invention, the long-acting conjugate of a glucagon derivative may exhibit increased persistence of efficacy compared to the native glucagon or glucagon derivative to which a carrier is not bound.

In an embodiment of the present invention, the long-acting conjugate may be a conjugate represented by the following Chemical Formula 1, but is not limited thereto:

X-L-F [Chemical Formula 1]

wherein X is the peptide described above;

L is a linker containing an ethylene glycol repeating unit;

F is an immunoglobulin Fc region; and

— represents linkage between X and L and between L and F by a covalent bond.

In the long-acting conjugate, X may be the peptide (glucagon derivative) according to the present invention. Specifically, X may be a peptide including the amino acid sequence represented by Formula 1, or X may be a peptide including an amino acid sequence of any one of SEQ ID NOs: 2 to 11 and 13 to 45, or X may be a peptide including an amino acid sequence selected from the group consisting of SEQ ID NOs: 20, 22, 23, 27, 33, 35, 37, 38, 40, 41, 42, and 44, but is not limited thereto.

In the long-acting conjugate, F is X, namely, a substance capable of increasing the half-life of glucagon derivative, and corresponds to one component of the moiety constituting the conjugate of the present invention.

F may be bound to X by a covalent chemical bond or a non-covalent chemical bond, specifically bound to X via L by a covalent chemical bond.

As a specific example, F may be an immunoglobulin Fc region, and more specifically the immunoglobulin Fc region may be derived from IgG, but F is not particularly limited thereto.

As used herein, the term "immunoglobulin Fc region" refers to a site including heavy chain constant region 2 (CH2) and/or heavy chain constant region 3 (CH3) except for the heavy and light chain variable regions of immunoglobulin. The immunoglobulin Fc region may be one component constituting a moiety of the protein conjugate of the present invention.

As used herein, the term Fc fragment includes not only the native sequence obtained from papain digestion of immunoglobulin, but also a derivative thereof, for example, a sequence in which one or more amino acid residues in the native sequence are changed by deletion, insertion, non-conservative or conservative substitution, or a combination thereof to be different from the native sequence.

F is a structure in which two polypeptide chains are linked by a disulfide bond, and may be a structure in which only one of the two chains is linked through a nitrogen atom, but is not limited thereto. The linkage through a nitrogen atom may be achieved through reductive amination of the epsilon amino atom or N-terminal amino group of lysine.

Reductive amination reaction refers to a reaction in which an amine group or amino group of a reactant reacts with an aldehyde (namely, a functional group capable of undergoing reductive amination) of another reactant to produce an amine and then an amine bond is formed by a reduction reaction, and is an organic synthesis reaction widely known in the art.

As an embodiment, F may be linked through a nitrogen atom of the N-terminal proline, but is not limited thereto.

Such an immunoglobulin Fc fragment may include a hinge region in the heavy chain constant region, but is not limited thereto.

In the present invention, the immunoglobulin Fc fragment may include a specific hinge sequence at the N-terminus.

As used herein, the term "hinge sequence" refers to a site that is located on a heavy chain and forms a dimer of an immunoglobulin Fc fragment through an inter-disulfide bond.

In the present invention, the hinge sequence may be mutated to have only one cysteine residue by deleting a part of a hinge sequence having the following amino acid sequence, but is not limited thereto:

```
                                     (SEQ ID NO: 51)
Glu-Ser-Lys-Tyr-Gly-Pro-Pro-Cys-Pro-Ser-Cys-Pro.
```

The hinge sequence may include only one cysteine residue by deleting the 8th or 11th cysteine residue in the hinge sequence of SEQ ID NO: 51. The hinge sequence of the present invention may be composed of 3 to 12 amino acids including only one cysteine residue, but is not limited thereto. More specifically, the hinge sequence of the present invention may have the following sequence:

```
                                     (SEQ ID NO: 52)
Glu-Ser-Lys-Tyr-Gly-Pro-Pro-Pro-Ser-Cys-Pro,

                                     (SEQ ID NO: 53)
Glu-Ser-Lys-Tyr-Gly-Pro-Pro-Cys-Pro-Ser-Pro,

                                     (SEQ ID NO: 54)
Glu-Ser-Lys-Tyr-Gly-Pro-Pro-Cys-Pro-Ser,

                                     (SEQ ID NO: 55)
Glu-Ser-Lys-Tyr-Gly-Pro-Pro-Cys-Pro-Pro,

                                     (SEQ ID NO: 56)
Lys-Tyr-Gly-Pro-Pro-Cys-Pro-Ser,

                                     (SEQ ID NO: 57)
Glu-Ser-Lys-Tyr-Gly-Pro-Pro-Cys,

                                     (SEQ ID NO: 58)
Glu-Lys-Tyr-Gly-Pro-Pro-Cys.

                                     (SEQ ID NO: 59)
Glu-Ser-Pro-Ser-Cys-Pro,

                                     (SEQ ID NO: 60)
Glu-Pro-Ser-Cys-Pro,

                                     (SEQ ID NO: 61)
Pro-Ser-Cys-Pro,

                                     (SEQ ID NO: 62)
Glu-Ser-Lys-Tyr-Gly-Pro-Pro-Ser-Cys-Pro,

                                     (SEQ ID NO: 63)
Lys-Tyr-Glypro-Pro-Pro-Ser-Cys-Pro,

                                     (SEQ ID NO: 64)
Glu-Ser-Lys-Tyr-Gly-Pro-Ser-Cys-Pro,

                                     (SEQ ID NO: 65)
Glu-Ser-Lys-Tyr-Gly-Pro-Pro-Cys,

                                     (SEQ ID NO: 66)
Lys-Tyr-Gly-Pro-Pro-Cys-Pro,

                                     (SEQ ID NO: 67)
Glu-Ser-Lys-Pro-Ser-Cys-Pro,

                                     (SEQ ID NO: 68)
Glu-Ser-Pro-Ser-Cys-Pro,
```

-continued

```
                                     (SEQ ID NO: 69)
Glu-Pro-Ser-Cys,
or

                                     (SEQ ID NO: 70)
Ser-Cys-Pro.
```

More specifically, the hinge sequence may include the amino acid sequence of SEQ ID NO: 61 (Pro-Ser-Cys-Pro) or SEQ ID NO: 70 (Ser-Cys-Pro), but is not limited thereto.

The immunoglobulin Fc fragment of the present invention may be in a form in which two molecules of immunoglobulin Fc chain form a dimer due to the presence of a hinge sequence, and the conjugate represented by Chemical Formula 1 of the present invention may be in a form in which one terminus of the linker is linked to one chain of the dimer immunoglobulin Fc fragment, but is not limited thereto.

As used herein, the term "N-terminus" refers to an amino terminus of a protein or polypeptide, and may include the most end of amino terminus, or 1, 2, 3, 4, 5, 6, 7, 8, 9, or 10 or more amino acids from the most end. The immunoglobulin Fc fragment of the present invention may include a hinge sequence at the N-terminus, but is not limited thereto.

The immunoglobulin Fc fragment of the present invention may be an extended Fc fragment including a part or all of the heavy chain constant region 1 (CH1) and/or the light chain constant region 1 (CL1) except for only the heavy and light chain variable regions of immunoglobulin as long as it has an effect substantially equivalent to or enhanced than that of the native type. The immunoglobulin Fc fragment may be a fragment in which some fairly long amino acid sequences corresponding to CH2 and/or CH3 are removed.

For example, the immunoglobulin Fc region of the present invention may be 1) CH1 domain, CH2 domain, CH3 domain, and CH4 domain; 2) CH1 domain and CH2 domain; 3) CH1 domain and CH3 domain; 4) CH2 domain and CH3 domain; 5) a combination of one or two or more domains of CH1 domain, CH2 domain, CH3 domain, or CH4 domain with an immunoglobulin hinge region (or a part of a hinge region); or 6) a dimer of each domain of the heavy chain constant region and the light chain constant region. However, the immunoglobulin Fc region is not limited thereto.

In an embodiment, the immunoglobulin Fc region may be in a dimeric form, and one molecule of glucagon derivative may be covalently linked to one Fc region in the dimeric form. In this case, the immunoglobulin Fc and the glucagon derivative may be linked to each other by a non-peptidyl polymer. It is also possible for two molecules of glucagon derivative to bind symmetrically to one Fc region in the dimer form. In this case, the immunoglobulin Fc and the glucagon derivative or the insulin-secreting peptide may be linked to each other by a non-peptidyl linker. However, the immunoglobulin Fc region is not limited to the examples described above.

The immunoglobulin Fc region of the present invention includes a native amino acid sequence as well as a sequence derivative of the same. An amino acid sequence derivative means that one or more amino acid residues in a native amino acid sequence have a different sequence by deletion, insertion, non-conservative or conservative substitution, or a combination thereof.

For example, in the case of IgG Fc, amino acid residues 214 to 238, 297 to 299, 318 to 322, or 327 to 331, which are known to be important for binding, may be used as suitable sites for modification.

Various kinds of derivatives are possible in which a site capable of forming a disulfide bond may be removed, some amino acids at the N-terminus may be removed from native Fc, or a methionine residue may be added to the N-terminus of native Fc. In order to eliminate the effector function, the complement binding site, for example, the C1q binding site may be removed or the ADCC (antibody dependent cell mediated cytotoxicity) site may be removed. Techniques for preparing such sequence derivatives of immunoglobulin Fc region are disclosed in International Patent Publication No. WO 97/34631 and International Patent Publication No. 96/32478.

Amino acid exchanges in proteins and peptides that do not entirely alter the molecule activity are known in the art (H. Neurath, R. L. Hill, *The Proteins*, Academic Press, New York, 1979). The most commonly occurring exchange is exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ille, Leu/Val, Ala/Glu, and Asp/Gly. In some cases, modification may be performed by phosphorylation, sulfation, acrylation, glycosylation, methylation, farnesylation, acetylation, amidation, and the like.

The above-described Fc derivatives may exhibit biologic activity equivalent to that of the Fc region of the present invention and enhanced structural stability of the Fc region to heat, pH and the like.

Such an Fc region may be obtained from a native type isolated in vivo from animals such as humans, cows, goats, pigs, mice, rabbits, hamsters, rats, or guinea pigs, or may be a recombinant obtained from a transformed animal cell or microorganism or a derivative thereof. Here, the method for obtaining an Fc region from the native type may be a method in which the whole immunoglobulin is isolated in vivo from a human or an animal and then treated with a proteolytic enzyme. The whole immunoglobulin is cleaved into Fab and Fc when treated with papain, and cleaved into pF'c and $F(ab)_2$ when treated with pepsin. Fc or pF'c may be isolated by size-exclusion chromatography or the like. In a more specific embodiment, the Fc region is a recombinant immunoglobulin Fc region that is a human-derived Fc region obtained from a microorganism.

The immunoglobulin Fc region may have a native sugar chain, an increased sugar chain compared to the native type, a decreased sugar chain compared to the native type, or a deglycosylated form. For the increase or decrease or removal of such immunoglobulin Fc sugar chains, conventional methods such as chemical methods, enzymatic methods, and genetic engineering methods using microorganisms may be used. Here, the immunoglobulin Fc region in which sugar chains are removed from Fc does not induce an unnecessary immune response in vivo since its binding affinity to complement (c1q) is significantly reduced and antibody-dependent cytotoxicity or complement-dependent cytotoxicity is reduced or eliminated. In this regard, a form more suitable for the intended purpose as a drug carrier is a deglycosylated or aglycosylated immunoglobulin Fc region.

In the present invention, "deglycosylation" refers to an Fc region from which sugars are removed with an enzyme, and aglycosylation refers to an Fc region that is not glycosylated by being produced from a prokaryote, in a more specific embodiment, *E. coli.*

The immunoglobulin Fc region may be of human or animal origin, such as cattle, goats, pigs, mice, rabbits, hamsters, rats, or guinea pigs, and is of human origin in a more specific embodiment.

The immunoglobulin Fc region may be an Fc region derived from IgG, IgA, IgD, IgE, or IgM or by a combination thereof or a hybrid thereof. The immunoglobulin Fc region is, in a more specific embodiment, derived from IgG or IgM that is most abundant in human blood and, in a still more specific embodiment, derived from IgG that is known to enhance the half-life of ligand binding proteins. In a yet still more specific embodiment, the immunoglobulin Fc region is an IgG4 Fc region. In the most specific embodiment, the immunoglobulin Fc region is an aglycosylated Fc region derived from human IgG4, but is not limited thereto.

In a specific embodiment, the immunoglobulin Fc fragment is a fragment of human IgG4 Fc, may be in the form of a homodimer in which two monomers are linked through a disulfide bond (inter-chain form) between cysteine, the third amino acid of each monomer. In this case, each monomer of the homodimer independently have/may have an internal disulfide bond between cysteines at positions 35 and 95 and an internal disulfide bond between cysteines at positions 141 and 199, namely two disulfide bonds (intra-chain form). The number of amino acids of each monomer may be 221, and the amino acids forming the homodimer may consist of a total of 442 amino acids, but the number of amino acids is not limited thereto. Specifically, in the immunoglobulin Fc fragment, two monomers having the amino acid sequence of SEQ ID NO: 71 (consisting of 221 amino acids) form a homodimer through an inter-disulfide bond between cysteines, the third amino acid of each monomer, and the monomers of the homodimer may each independently form a disulfide bond between cysteines at positions 35 and 95 and a disulfide bond between cysteines at positions 141 and 199, but the immunoglobulin Fc fragment is not limited thereto.

In the present invention, "combination" means that polypeptides encoding single-chain immunoglobulin Fc regions of the same origin form bonds with single-chain polypeptides of different origins when a dimer or multimer is formed. In other words, a dimer or multimer can be prepared from two or more fragments selected from the group consisting of IgG Fc, IgA Fc, IgM Fc, IgD Fc, and IgE Fc fragments.

L may be a non-peptidyl linker, for example, a linker containing an ethylene glycol repeating unit.

In the present invention, "non-peptidyl linker" includes a biocompatible polymer in which two or more repeating units are bound. The repeating units are bound to each other through any covalent bond other than a peptide bond. The non-peptidyl linker may be one component constituting a moiety of the conjugate of the present invention, and corresponds to L in Chemical Formula 1. As the non-peptidyl linker that can be used in the present invention, any polymer resistant to in vivo proteolytic enzymes may be used without limitation. In the present invention, the non-peptidyl linker may be used interchangeably with a non-peptidyl polymer.

Although not particularly limited thereto, the non-peptidyl linker may be a linker containing an ethylene glycol repeating unit, for example, polyethylene glycol, and derivatives thereof already known in the art and derivatives that can be easily prepared at the level of skill in the art are also included in the scope of the present invention.

The repeating unit of the non-peptidyl linker may be an ethylene glycol repeating unit. Specifically, the non-peptidyl linker may include an ethylene glycol repeating unit and a functional group used in the preparation of the conjugate at the terminus. The long-acting conjugate according to the present invention may be in a form in which X and F are linked through the functional group, but is not limited thereto. In the present invention, the non-peptidyl linker may include two or three or more functional groups, and the respective functional groups may be the same as or different from each other, but the non-peptidyl linker is not limited thereto.

Specifically, the linker may be polyethylene glycol (PEG) represented by the following Chemical Formula 2, but is not limited thereto:

[Chemical Formula 2]

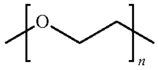

where, n=10 to 2400, n=10 to 480, or n=50 to 250, but is not limited thereto.

The PEG moiety in the long-acting conjugate may include not only the $-(CH_2CH_2O)_n-$, structure but also an oxygen atom interposed between the linkage element and $-(CH_2CH_2O)_n-$, but is not limited thereto.

In a specific embodiment, the conjugate may have a structure in which the glucagon derivative peptide or the peptide (X) including the amino acid sequence represented by Formula 1 and the immunoglobulin fragment (F) are covalently linked through a linker containing an ethylene glycol repeating unit, but is not limited thereto. The polyethylene glycol is a term that encompasses all forms of ethylene glycol homopolymer, PEG copolymer, and monomethyl-substituted PEG polymer (mPEG), but is not particularly limited thereto. Specifically, the chemical formula weight of the ethylene glycol repeating unit moiety in L may be in a range of 1 kDa to 100 kDa, but is not limited thereto.

The molecular weight of the non-peptidyl polymer is in a range of 1 kDa to 100 kDa, specifically in a range of 1 kDa to 20 kDa, or in a range of 1 kDa to 10 kDa, but is not limited thereto. As the non-peptidyl linker of the present invention bound to the polypeptide corresponding to F, not only one kind of polymer but also a combination of different kinds of polymers may be used.

In a specific embodiment, both terminuses of the non-peptidyl linker may bind to an amine or thiol group of F, for example, an immunoglobulin Fc fragment and an amine or thiol group of X, respectively.

Specifically, the non-peptidyl polymer may include a reactive group capable of binding to F (for example, an immunoglobulin Fc fragment) and X, specifically a reactive group capable of binding to an amine group located at the N-terminus or lysine or a thiol group of cysteine of X or F at both terminuses, but is not limited thereto.

The reactive group of the non-peptidyl polymer, which can bind to F, for example, an immunoglobulin Fc fragment and X, may be selected from the group consisting of an aldehyde group, a maleimide group and a succinimide derivative, but is not limited thereto.

In the above, examples of the aldehyde group include a propionaldehyde group or a butyraldehyde group, but the aldehyde group is not limited thereto.

In the above, as the succinimide derivative, succinimidyl valerate, succinimidyl methylbutanoate, succinimidyl methylpropionate, succinimidyl butanoate, succinimidyl propionate, N-hydroxysuccinimide, hydroxysuccinimide, succinimidyl carboxymethyl or succinimidyl carbonate may be used, but the succinimide derivative is not limited thereto.

The non-peptidyl linker may be linked to X and F through such a reactive group, but is not particularly limited thereto.

The final product produced by reductive amination through an aldehyde bond is far more stable than those linked by an amide bond. The aldehyde reactive group selectively reacts with the N-terminus at a low pH, and may form a covalent bond with a lysine residue at a high pH, for example, pH 9.0.

The reactive groups at both terminuses of the non-peptidyl linker may be the same as or different from each other. For example, the non-peptidyl linker may have a maleimide group at one terminus and an aldehyde group, a propionaldehyde group, or a butyraldehyde group at the other terminus. However, the non-peptidyl linker is not particularly limited thereto as long as F, specifically an immunoglobulin Fc fragment and X can be bound to each terminus of the non-peptidyl linker.

For example, one terminus of the non-peptidyl linker may include a maleimide group as a reactive group, and the other terminus may include an aldehyde group, a propionaldehyde group, or a butyraldehyde group.

In the case of using polyethylene glycol having a hydroxy reactive group at both terminuses as a non-peptidyl polymer, the long-acting protein conjugate of the present invention may be prepared by activating the hydroxyl group into the various reactive groups by a known chemical reaction, or using commercially available polyethylene glycol having a modified reactive group.

In a specific embodiment, the non-peptidyl polymer may be linked to a cysteine residue of X, more specifically a —SH group of cysteine, but is not limited thereto.

Specifically, a reactive group of the non-peptidyl polymer may be linked to the —SH group of the cysteine residue, and all of the above descriptions apply to the reactive group. When maleimide-PEG-aldehyde is used, the maleimide group may be linked to the —SH group of X by a thioether bond, and the aldehyde group may be linked to F, specifically $-NH_2$ group of immunoglobulin Fc through reductive amination reaction, but the conjugate is not limited thereto, and this corresponds to an example.

In the conjugate, the reactive group of the non-peptidyl polymer may be linked to $-NH_2$ located at the N-terminus of the immunoglobulin Fc fragment, but this corresponds to an example.

The above-described conjugate may exhibit enhanced persistence of efficacy compared to native glucagon or compared to X that is not modified with F, and such a conjugate includes not only the above-described forms but also a form encapsulated in biodegradable nanoparticles.

The GLP-1 and GIP receptor dual agonist of the present invention includes various substances exhibiting significant levels of activity with respect to the GLP-1 receptor and the GIP receptor, for example, substances in the form of compounds or peptides. The GLP-1 and GIP receptor dual agonist herein may be used interchangeably with "GLP-1/GIP dual agonist", or "dual agonist".

Specifically, the dual agonist possesses one or more of the following activities i) to ii), in particular significant activity:

i) activation of the GLP-1 receptor; and ii) activation of the GIP receptor.

Although not particularly limited thereto, the GLP-1 (glucagon-like peptide-1) and GIP (glucose-dependent insulinotropic polypeptide) receptor dual agonist is a substance exhibiting a significant level of activity with respect to the receptors, and may exhibit in vitro activity with respect to native GLP-1 and GIP as well as the GLP-1 receptor and the GIP receptor to be 0.1% or more, 1% or more, 2% or more, 3% or more, 4% or more, 5% or more, 6% or more, 7% or more, 8% or more, 9% or more, 10% or more, 20% or more, 30% or more, 40% or more, 50% or more, 60% or more, 70% or more, 80% or more, 90% or more, 100% or more of those of native ligands (native GLP-1 and GIP) of the corresponding receptors, but significantly increased ranges are included without limitation.

The method for measuring the in vitro activity of such a dual agonist may be achieved by various in vitro activity measurements known in the art, and Example 2 of the present specification may be referred to as an example, but the method is not particularly limited thereto.

Although not particularly limited thereto, the dual agonist may be a dual agonist which does not occur naturally.

Examples of the substance exhibiting activity with respect to the GLP-1 receptor and the GIP receptor include native GLP-1 and GIP, agonists thereof, or derivatives thereof, but are not particularly limited thereto. The "derivative" is as described above.

Although not particularly limited thereto, the GLP-1 and GIP receptor dual agonist may be a peptide exhibiting activity with respect to the GLP-1 receptor and the GIP receptor.

Specifically, the GLP-1 and GIP receptor dual agonist of the present invention is a derivative of GLP-1 or GIP that exhibits activity with respect to the GLP-1 receptor and the GIP receptor, and any GLP-1 and GIP receptor dual agonist known in the art may be included in the scope of the present invention without limitation. The GLP-1 and GIP receptor dual agonist according to the present invention may be a commercially available one or prepared by way of a method known in the art as long as it can exhibit activity with respect to the GLP-1 receptor and the GIP receptor. Examples of the GLP-1 and GIP receptor dual agonist include, but are not limited to, tirzepatide, NN9709, and SAR-438335.

Tirzepatide, an example of the GLP-1 and GIP receptor dual agonist according to the present invention, is known as L-tyrosyl-2-methylalanyl-L-α-glutamylglycyl-L-threonyl-L-phenylalanyl-L-threonyl-L-seryl-L-α-aspartyl-L-tyrosyl-L-seryl-L-isoleucyl-2-methylalanyl-L-leucyl-L-α-aspartyl-L-lysyl-L-isoleucyl-L-alanyl-L-glutaminyl-$N^6$-[(22S)-22,42-dicarboxy-10,19,24-trioxo-3,6,12,15-tetraoxa-9,18,23-triazadotetracontan-1-oyl]-L-lysyl-L-alanyl-L-phenylalanyl-L-valyl-L-glutaminyl-L-tryptophyl-L-leucyl-L-isoleucyl-L-alanylglycylglycyl-L-prolyl-L-seryl-L-serylglycyl-L-alanyl-L-prolyl-L-prolyl-L-prolyl-L-serinamide (CAS #2023788-19-2), and is a substance having the following sequence:

(SEQ ID NO: 50)
YXEGTFTSDY SIXLDKIAQK AFVQWLIAGG PSSGAPPPS wherein X, K, and S are each a residue modified as follows.

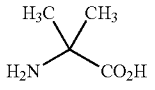

X (2, 13)
2-methylalanine (Aib)

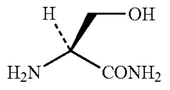

S (39)
L-serinamide

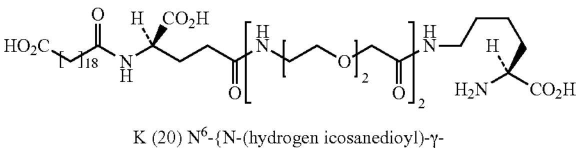

K (20) $N^6$-{N-(hydrogen icosanedioyl)-γ-Glu-bis[iminobis(ethylenoxy)acetyl]}-Lysine Although not particularly limited thereto, the GLP-1 and GIP receptor dual agonist of the present invention may be in a form in which a terminus is modified, specifically one in which one terminus of the dual agonist is acylated or amidated, but is not limited thereto.

The peptide of the present invention may be synthesized by way of a method well known in the art, for example, using an automatic peptide synthesizer according to its length, or may also be produced by genetic engineering techniques.

Specifically, the peptide of the present invention may be prepared by way of standard synthetic methods, recombinant expression systems, or any other method in the art. Hence, the peptides according to the present invention may be synthesized by way of a number of methods including, for example, the following methods:

(a) a method in which the peptide is synthesized stepwise or by fragment assembly by means of a solid or liquid phase method and the final peptide product is isolated and purified; or (b) a method in which a nucleic acid construct encoding the peptide is expressed in a host cell and the expressed product is recovered from the host cell culture; or (c) cell-free in vitro expression of a nucleic acid construct encoding the peptide is performed and the expressed product is recovered; or a method in which a fragment of the peptide is obtained by any combination of (a), (b), and (c), then the fragments are ligated to obtain a peptide, and the peptide is recovered.

As a more specific example, a polynucleotide encoding a peptide is prepared through genetic manipulation, and transformed into a host cell, and then a desired peptide may be produced.

Although not particularly limited thereto, in the composition of the present invention, the in vitro activity of glucagon derivate may be about 0.1% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, or about 100% or more compared to the native ligand activity of the glucagon receptor, and in the case of the GLP-1 and GIP receptor dual agonist, the in vitro activity of GLP-1 may be about 0.1% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, or about 100% or more compared to the native ligand activity of the GLP-1 receptor, and the in vitro activity of GIP may be about 0.1% or more, about 1% or more, about 2% or more, about 3% or more, about 4% or more, about 5% or more, about 6% or more, about 7% or more, about 8% or more, about 9% or more, about 10% or more, about 20% or more, about 30% or more, about 40% or more, about 50% or more, about 60% or more, about 70% or more, about 80% or more, about 90% or more, or about 100% or more compared to the native ligand activity of the GIP receptor, but the in vitro activity is not limited thereto. Although not particularly limited thereto, in the composition of the present invention, the in vitro activity of glucagon derivate may be about 0.1% or more and about 300% or less, about 2% or more and about 300% or less, about 3% or more and about 300% or less, about 4% or more and about 300% or less, about 5% or more and about 300% or less, about 6% or more and about 300% or less, about 7% or more and about 300% or less, about 8% or more and about 300% or less, about 9% or more and about 300% or less, about 10% or more and about 300% or less, about 20% or more and about 300% or less, about 30% or more and about 300% or less, about 40% or more and about 300% or less, about 50% or more and about 300% or less, about 60% or more and about 300% or less, about 70% or more and about 300% or less, about 80% or more and about 300% or less, about 90% or more and about 300% or less, or about 100% or more and about 300% or less compared to the native ligand activity of the glucagon receptor, and in the case of the GLP-1 and GIP receptor dual agonist, the in vitro activity of GLP-1 may be about 0.1% or more and about 200% or less, about 2% or more and about 200% or less, about 3% or more and about 200% or less, about 4% or more and about 200% or less, about 5% or more and about 200% or less, about 6% or more and about 200% or less, about 7% or more and about 200% or less, about 8% or more and about 200% or less, about 9% or more and about 200% or less, about 10% or more and about 200% or less, about 20% or more and about 200% or less, about 30% or more and about 200% or less, about 40% or more and about 200% or less, about 50% or more and about 200% or less, about 60% or more and about 200% or less, about 70% or more and about 200% or less, about 80% or more and about 200% or less, about 90% or more and about 200% or less, or about 100% or more and about 200% or less compared to the native ligand activity of the GLP-1 receptor, and the in vitro activity of GIP may be about 0.1% or more and about 300% or less, about 2% or more and about 300% or less, about 3% or more and about 300% or less, about 4% or more and about 300% or less, about 5% or more and about 300% or less, about 6% or more and about 300% or less, about 7% or more and about 300% or less, about 8% or more and about 300% or less, about 9% or more and about 300% or less, about 10% or more and about 300% or less, about 20% or more and about 300% or less, about 30% or more and about 300% or less, about 40% or more and about 300% or less, about 50% or more and about 300% or less, about 60% or more and about 300% or less, about 70% or more and about 300% or less, about 80% or more and about 300% or less, about 90% or more and about 300% or less, or about 100% or more and about 300% or less compared to the native ligand activity of the GIP receptor, but the in vitro activity is not limited thereto.

The composition of the present invention may be used for the prevention or treatment of metabolic syndrome.

As used herein, the term "prevention" refers to any action that inhibits or delays the onset of a target disease, for example, metabolic syndrome, by administration of (i) a substance exhibiting glucagon activity, and (ii) a GLP-1 and GIP receptor dual agonist; or a composition comprising these, and the term "treatment" refers to any action that improves or benefit the symptoms of a target disease, for example, metabolic syndrome by administration of (i) a substance exhibiting glucagon activity, and (ii) a GLP-1 and GIP receptor dual agonist; or a composition comprising these.

As used herein, the term "administration" means introducing a predetermined substance to a patient by any suitable method, and the route of administration of the composition is not particularly limited thereto, but the composition may be administered through any general route through which the composition can reach an in vivo target, and the administration may be, for example, intraperitoneal administration, intravenous administration, intramuscular administration, subcutaneous administration, intradermal administration, oral administration, topical administration, intranasal administration, intrapulmonary administration, and rectal administration.

The substance exhibiting glucagon activity and the GLP-1 and GIP receptor dual agonist may be used for the prevention or treatment of metabolic syndrome.

The combined administration of (i) the substance exhibiting glucagon activity and (ii) the GLP-1 and GIP receptor dual agonist of the present invention not only prevents body weight gain, promotes body weight loss, reduces excess body weight, or shows an effect on obesity including morbid obesity (for example, by regulation of appetite, feeding, food intake, caloric intake and/or energy expenditure) but is also effective in diseases including obesity-related inflammation, obesity-related gallbladder disease, and obesity-induced sleep apnea. The combined administration of (i) the substance exhibiting glucagon activity and (ii) the GLP-1 and GIP receptor dual agonist of the present invention may also be effective in metabolic syndrome or obesity-related liver disease, but the substance exhibiting glucagon activity and the GLP-1 and GIP receptor dual agonist may be used as a medicament for treating related diseases that are not limited thereto and health conditions. The substance exhibiting glucagon activity and the GLP-1 and GIP receptor dual agonist of the present invention may also be used for the treatment of metabolic syndrome other than obesity, namely related diseases such as impaired glucose tolerance, hypercholesterolemia, dyslipidemia, obesity, diabetes, hypertension, liver disease, arteriosclerosis caused by dyslipidemia, atherosclerosis, arteriosclerosis, coronary artery heart disease (coronary heart disease), and stroke. However, the effect of the substance exhibiting glucagon activity and the GLP-1 and GIP receptor dual agonist according to the present invention on these conditions may be mediated in whole or in part through the aforementioned body weight related effects or may be independent of this.

As used herein, the term "metabolic syndrome" refers to symptoms in which various diseases caused by chronic metabolic disorders occur singly or in a complex manner. In particular, diseases corresponding to metabolic syndrome include, but are not limited to, impaired glucose tolerance, hypercholesterolemia, dyslipidemia, obesity, diabetes, hypertension, liver disease, arteriosclerosis caused by dyslipidemia, atherosclerosis, arteriosclerosis, coronary artery heart disease (coronary heart disease), and stroke.

In the present invention, the term "obesity" refers to a state in which adipose tissue is excessive in the body, and it is defined as obesity when the body mass index (weight (kg) divided by height (m) squared) is 25 or more. Obesity is usually caused by energy imbalance due to excessive intake of nutrients compared to energy expenditure over a long period of time. Obesity is a metabolic disease that affects the entire body, increases the risk of diabetes and hyperlipidemia, sexual dysfunction, arthritis, and cardiovascular disease, and is also associated with cancer in some cases. The treatment of obesity may be achieved through body weight and body fat loss, but is not limited thereto.

As used herein, the term "hyperlipidemia" refers to a state in which lipids such as free cholesterol, cholesterol esters, phospholipids, and triglycerides are abnormally increased in the blood. Hyperlipidemia does not usually show specific symptoms by itself, but excess lipids in the blood adhere to the walls of blood vessels, reduce the size of blood vessels, and cause atherosclerosis through an inflammatory response. This may lead to coronary heart disease, cerebrovascular disease, and occlusion of peripheral blood vessels. Excess lipids in the blood accumulates in the liver tissue, and this may cause fatty liver. In the above, fatty liver refers to a state in which the proportion of fat in the weight of the liver exceeds 5%, and may be caused by alcohol intake as well as excessive fat intake. The treatment of hyperlipidemia may be achieved through improvement of blood lipid levels, but is not limited thereto.

As used herein, the term "diabetes" refers to a kind of metabolic disease such as insufficient insulin secretion or failure to function normally, and is characterized by high blood sugar in which the concentration of blood sugar increases. Recently, the incidence of diabetes has been explosively increasing due to an increase in the obesity rate, particularly abdominal obesity. If a chronic hyperglycemic condition is not suitably treated, it leads to various pathological conditions in the body. Typically, it increases the risk of retinopathy, renal dysfunction, neuropathy, stroke caused by vascular disorder, kidney or heart diseases, diabetic foot ulcer, and cardiovascular disease. The treatment of diabetes may be achieved through improvement of blood sugar by improvement of insulin sensitivity, but is not limited thereto.

The above-described metabolic syndrome is closely related to the liver disease including the accumulation of fat in liver tissue and the resulting inflammation and fibrosis, and examples of metabolic syndrome may include various liver diseases.

Accordingly, the composition of the present invention may have a preventive or therapeutic use for liver disease. Specifically, the composition comprising (i) a substance exhibiting glucagon activity and (ii) a GLP-1 and GIP receptor dual agonist according to the present invention may have a preventive or therapeutic use for liver disease by exhibiting an effect of inhibiting and improving inflammation and/or fibrosis in liver tissue, but is not limited thereto.

As used herein, the term "liver disease" refers to a disease occurring in the liver, and may include metabolic liver disease, but is not limited thereto. Representative examples of the liver disease include simple steatosis, non-alcoholic fatty liver, liver inflammation, non-alcoholic steatohepatitis, cholestasis liver disease, liver fibrosis, liver cirrhosis, liver decompensation, and hepatocellular carcinoma, and it may be a liver disease according to the present invention as long as abnormalities occur in the tissue and function of the liver. In addition to alcohol consumption, drugs, and viral infections, obesity, metabolic disorders and the like may cause liver inflammation, and it is known that diseases such as liver cirrhosis and hepatocellular carcinoma occur according to the progression and chronicity of liver inflammation.

Specifically, the composition comprising (i) the substance exhibiting glucagon activity and (ii) the GLP-1 and GIP receptor dual agonist according to the present invention may exhibit a preventive or therapeutic effect on liver disease associated with metabolic syndrome or caused by metabolic syndrome.

The liver disease on which the composition comprising (i) the substance exhibiting glucagon activity and (ii) the GLP-1 and GIP receptor dual agonist according to the present invention exhibits a therapeutic effect may be metabolic liver disease, but is not limited thereto. Metabolic liver disease is a disease caused by an abnormal chemical reaction in the body that interferes with the body's metabolism, and includes simple steatosis, fatty liver, steatohepatitis, and non-alcoholic fatty liver disease.

In the present invention, "non-alcoholic fatty liver disease (NAFLD)" refers to a case that does not have history of alcohol intake or is not related to alcohol intake but is accompanied by fatty liver. Fatty liver refers to a phenomenon in which triglycerides are abnormally deposited in liver cells unlike normal cases. A normal liver consists of about 5% adipose tissue, and triglycerides, fatty acids, phospholipids, cholesterol and cholesterol esters are the main components of fat. Once fatty liver occurs, most of the components are replaced with triglycerides, and it is diagnosed as fatty liver when the amount of triglycerides is 5% or more of the liver weight. Fatty liver is caused by disorders of fat metabolism in liver cells or defects in the process of transporting excess fat, and is mainly caused by disorders of fat metabolism in the liver. Most of the fat accumulated in the fatty liver may be triglycerides.

Non-alcoholic fatty liver disease refers to a group of diseases including simple steatosis with only excessive accumulation of fat in liver cells, non-alcoholic fatty liver, and non-alcoholic steatohepatitis (NASH) accompanied by hepatocellular necrosis, inflammation, and fibrosis, but is not limited thereto as long as it is treated with the composition of the present invention. The non-alcoholic fatty liver disease according to the present invention may be accompanied by non-alcoholic steatohepatitis, but is not limited thereto.

The liver disease on which the composition comprising (i) the substance exhibiting glucagon activity and (ii) the GLP-1 and GIP receptor dual agonist according to the present invention exhibits a therapeutic effect may be liver inflammation, but is not limited thereto. In the present invention, "liver inflammation" refers to a disease that causes inflammation of the liver as the greatest cause of liver disease, and is divided into acute hepatitis and chronic hepatitis depending on the cause and symptoms. Liver inflammation is mainly caused by viruses, alcohol, drugs, immune abnormalities, and metabolic diseases.

The composition comprising (i) the substance exhibiting glucagon activity and (ii) the GLP-1 and GIP receptor dual agonist according to the present invention not only has the effect of alleviating the inflammation of the liver itself, but also may exhibit an effect on diseases accompanied by inflammation of the liver or caused by inflammation of the liver, for example, hepatitis, non-alcoholic steatohepatitis, and liver fibrosis.

In the present invention, "non-alcoholic steatohepatitis" is one of non-alcoholic fatty liver disease, and is a representative example of liver disease accompanied by liver cell necrosis, inflammation, and fibrosis. The composition comprising (i) the substance exhibiting glucagon activity and (ii) the GLP-1 and GIP receptor dual agonist according to the present invention may exhibit an effect on non-alcoholic steatohepatitis by inhibiting liver inflammation and fibrosis, specifically may exhibit an effect on non-alcoholic steatohepatitis accompanied by fatty liver, liver fibrosis or liver cirrhosis; or hepatocellular carcinoma caused by non-alcoholic steatohepatitis, but is not limited thereto.

Specifically, the composition comprising (i) the substance exhibiting glucagon activity and (ii) the GLP-1 and GIP receptor dual agonist of the present invention exhibits an effect of reducing NAS (NAFLD activity score), and this means a therapeutic effect on non-alcoholic steatohepatitis.

In the present invention, "liver fibrosis" refers to the formation of excessive fibrous connective tissue in organs or tissues during reparative or reactive processes as a result of the wound healing process for repeated liver damage. The chronicity and deepening of liver inflammation is known to be one of the causes. It is known that liver fibrosis is reversible unlike liver cirrhosis, is composed of thin fibrils, and does not have nodule formation, and the liver may be recovered to the normal condition when the cause of liver damage is eliminated. However, when this liver fibrosis process continues repeatedly, crosslinking between the extracellular matrix (ECM) increases and liver fibrosis progresses to irreversible liver cirrhosis with nodules. The composition according to the present invention may exhibit a preventive or therapeutic effect on liver fibrosis, specifically liver fibrosis accompanied by non-alcoholic steatohepatitis, but is not limited thereto.

Specifically, the composition comprising (i) the substance exhibiting glucagon activity and (ii) the GLP-1 and GIP receptor dual agonist of the present invention may exhibit an effect on liver fibrosis, specifically may prevent or treat liver fibrosis by reducing collagen expression in liver tissue.

In the present invention, "cholestasis" is a condition in which the flow of bile from the liver to the duodenum is slowed or blocked, and "cholestasis liver disease" means that bile formation inside the liver is disturbed by conditions such as various diseases, dilated jugular vein nutrition, or side effects of certain drugs (for example, some antibiotics). Common signs of cholestasis include fatigue, pruritus (itching), jaundice, and xanthomas (deposition of cholesterol-rich substances under the skin). The influence of cholestasis is severe and widespread, leading to exacerbation of liver disease into systemic disease, liver decompensation, and the need for liver transplantation. Causes of cholestasis liver disease include acute hepatitis and bile duct inflammation.

The cholestasis liver disease may include primary biliary cholangitis (PBC), primary sclerosing cholangitis (PSC), progressive familial intrahepatic cholestasis (PFIC), and Alagille syndrome (AS), but is not limited thereto.

Primary biliary cirrhosis, also known as primary biliary cholangitis (PBC), is a chronic cholestasis liver disease of unknown etiology. Progressive bile duct damage due to portal and periportal inflammation may lead to progressive fibrosis and eventual cirrhosis of the liver. Thus far, immunological, genetic and environmental factors are known as potential causes of the disease. Primary biliary cirrhosis is mainly seen in middle-aged women, and the symptoms of primary biliary cirrhosis at early stage may also be fatigue, itching, or unexplained hyperlipidemia.

PBC is known so far as an immune-mediated disease of primary biliary sclerosis. Specifically, immunohistochemical staining of T lymphocytes in the portal vein and periportal regions reveals CD4-positive and CD8-negative T cells. Abnormal suppressor T-cell activity has been reported in asymptomatic Grade 1-relatives of affected individuals. It has been reported that interleukins may play a role in the pathogenesis of PBC by contributing to altered immune function and fibrosis (G. J. Webb et al., *J. Autoimmunity,* 2015 November; 64:42-52).

The treatment method for PBC is bile acid therapy using ursodeoxycholic acid (UDCA) and obeticholic acid (OCA). The mechanism of action of both drugs in PBC is associated with their ability to activate FXR and TGFR-5 to exert anti-inflammatory effects. However, sufficient biochemical responses have not been achieved in about 40% of patients treated with UDCA.

Primary sclerosing cholangitis (PSC) is a chronic progressive cholestasis liver disease caused by inflammation and fibrosis of the intrahepatic/extrahepatic biliary tract of unknown etiology. Specifically, PSC is an inflammatory disease of the bile duct and biliary tract, and fibrosis occurs and the bile duct wall thickens and narrows to cause biliary stricture as the disease progresses. Although the cause of PSC is still unknown, it is estimated that various factors such as genetic factors, environmental factors, and immune responses related thereto are a complex cause.

It is diagnosed as primary sclerosing cholangitis when elevated alkaline phosphatase levels, elevated aminotransferase levels, and gammaglobulinemia are observed in liver function tests using blood.

The treatment method for PSC has not yet been clearly reported, and liver transplantation is the only treatment method that can fundamentally treat PSC.

Accordingly, there is still a need to develop a drug capable of treating PBS and PSC without side effects while securing patient convenience.

"Liver cirrhosis" of the present invention is a chronic disease that occurs while hepatocyte regeneration and an increase in fibrous tissue repeatedly occur, is pathologically accompanied by necrosis, inflammation and fibrosis, and ultimately leads to cirrhosis complications such as liver decompensation and diseases such as hepatocellular carcinoma, leading to death. Liver cirrhosis is asymptomatic especially at the early stages and is thus diagnosed only at a fairly advanced stage. It is required to quickly treat liver fibrosis, which is a condition before evolution to liver cirrhosis and the like. The composition according to the present invention may exhibit a preventive or therapeutic effect on liver cirrhosis, specifically liver cirrhosis accompanied by non-alcoholic steatohepatitis, but is not limited thereto.

"Liver decompensation" of the present invention refers to a state in which liver function is weakened and the liver cannot perform protein synthesis and metabolic functions as normal physiological functions because of liver damage or liver disease such as viral hepatitis, cirrhosis, drugs or alcohol. Liver decompensation is classified into acute liver decompensation or chronic liver decompensation depending on the rate of progression, and is known to cause various complications. The composition according to the present invention exhibits effects such as inhibition of inflammation and fibrosis, and may thus exhibit a preventive or therapeutic effect on liver decompensation.

"Hepatocellular carcinoma" of the present invention refers to a malignant tumor originating in liver cells, and may be divided into primary liver cancer (hepatocellular carcinoma) that starts in hepatocytes itself and metastatic cancer of liver that has spread to the liver from a cancer that started in another tissue, and 90% or more of liver cancers are primary liver cancer. In addition to hepatitis and chronic liver disease, alcohol, smoking, and obesity are known to be the main causes of liver cancer. The composition according to the present invention may exhibit a preventive or therapeutic effect on hepatocellular carcinoma, specifically hepatocellular carcinoma caused by non-alcoholic steatohepatitis, but is not limited thereto.

In Examples of the present invention, a high-fat diet-induced obese mouse and a mouse model induced by CD-HFD (choline-deficient and high-fat, high-cholesterol diet) were used. The CD-HFD diet-induced model has high fat and cholesterol contents, and thus may cause fatty liver and steatohepatitis when ingested for a long period of time. It is known that a choline deficiency may aggravate such steatohepatitis and even lead to fibrosis.

In Examples of the present invention, the effect of the composition comprising (i) the substance exhibiting glucagon activity and (ii) the GLP-1 and GIP receptor dual agonist of the present invention has been examined in each of the models, and the results suggest that the composition is useful for preventing or treating metabolic syndrome and liver diseases such as liver fibrosis, simple steatosis, fatty liver, and non-alcoholic steatohepatitis.

The composition according to the present invention may be one that performs one or more of the following properties, but is not limited thereto:

(a) body weight and fat weight loss;
(b) improving blood lipid levels;
(c) improving insulin sensitivity;
(d) reducing UCP-1 and PGC-1a gene expression:
(e) reducing NAS (NAFLD activity score); and
(f) reducing collagen expression in liver tissue.

The composition according to the present invention may have no or a relatively low degree of body weight gain, which is a side effect of the existing therapeutic agents for liver disease.

The pharmaceutical composition of the present invention may further comprise a pharmaceutically acceptable carrier, excipient or diluent. As used herein, the term "pharmaceutically acceptable" means an amount sufficient to exhibit a therapeutic effect but not to cause side effects, and may be readily determined by those skilled in the art according to factors well known in the medical field, such as kind of disease, patient's age, weight, health, sex, and sensitivity to drugs, administration route, administration method, number of administrations, treatment period, and drugs blended or used simultaneously.

The pharmaceutical composition comprising a substance exhibiting glucagon activity and a GLP-1 and GIP receptor dual agonist of the present invention may further comprise a pharmaceutically acceptable carrier. The carrier is not particularly limited thereto, but a binder, a lubricant, a disintegrant, an excipient, a solubilizer, a dispersing agent, a stabilizer, a suspending agent, a colorant, a fragrance and the like may be used at the time of oral administration, a buffer, a preservative, an analgesic, a solubilizer, an isotonic agent, a stabilizer and the like may be used in mixture in the case of injections, and a base, an excipient, a lubricant, a preservative and the like may be used for topical administration.

The formulation of the composition of the present invention may be prepared in various forms by mixing with the pharmaceutically acceptable carriers as described above. For example, the composition may be prepared in the form of a tablet, a troche, a capsule, an elixir, a suspension, a syrup, a wafer, and the like at the time of oral administration, and in the form of unit dosage ampoules or multiple dosage forms in the case of injections. In addition, the composition may be formulated as a solution, a suspension, a tablet, a pill, a capsule, a sustained-release preparation, and the like.

As examples of carriers, excipients and diluents suitable for formation of preparations, lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, or mineral oil may be used. The preparations may further contain a filler, an anti-aggregation agent, a lubricant, a wetting agent, a flavoring agent, a preservative, and the like.

The pharmaceutical composition of the present invention may have any one formulation selected from the group consisting of a tablet, a pill, a powder, a granule, a capsule, a suspension, an oral liquid, an emulsion, a syrup, a sterilized aqueous solution, a non-aqueous solvent, a freeze-dried preparation, and a suppository.

The composition may be formulated in the form of a preparation for unit dosage form suitable for administration into the body of a patient according to a conventional method in the pharmaceutical field, specifically in the form of a preparation useful for the administration of peptide pharmaceuticals and administered by an oral administration route or a parenteral administration route including a dermal, intravenous, intramuscular, intraarterial, intramedullary, intrathecal, intraventricular, pulmonary, transdermal, subcutaneous, intraperitoneal, intranasal, gastrointestinal, topical, sublingual, intravaginal, or rectal route by way of an administration method commonly used in the art, but the formulation method and administration method are not limited thereto.

The substance exhibiting glucagon activity and the GLP-1 and GIP receptor dual agonist may be used by mixing with various pharmaceutically acceptable carriers such as physiological saline or organic solvents, and in order to increase the stability or absorption, carbohydrates such as glucose, sucrose or dextran, antioxidants such as ascorbic acid or glutathione, chelating agents, low-molecular-weight proteins, or other stabilizers may be used as agents.

The dosage and number of administrations of the pharmaceutical composition of the present invention are determined depending on the kind of drug as an active ingredient together with several related factors such as the disease to be treated, administration route, patients age, sex and weight, and severity of disease.

Although not particularly limited thereto, the pharmaceutical composition of the present invention may contain the component (active ingredient) at 0.01% to 99% by weight to volume.

The total effective amount of the composition of the present invention may be administered to a patient in a single dose, and may be administered by a fractionated treatment protocol in which multiple doses are administered over a long period of time. The pharmaceutical composition of the present invention may contain the active ingredient in a different amount depending on the severity of the disease. Specifically, a preferred total dose of the substance exhibiting glucagon activity and the GLP-1 and GIP receptor dual agonist of the present invention may be about 0.0001 μg to 500 mg/kg of patient body weight per day.

Specifically, the composition of the present invention may comprise the substance exhibiting glucagon activity at 0.15 nmol/kg to 2.5 nmol/kg, 0.19 nmol/kg to 2.25 nmol/kg, 0.25 nmol/kg to 1.5 nmol/kg, 0.37 nmol/kg to 1.12 nmol/kg and the GLP-1 and GIP receptor dual agonist at 2.0 nmol/kg to 35 nmol/kg, 2.08 nmol/kg to 31.16 nmol/kg, 10.39 nmol/kg to 31.16 nmol/kg, more specifically the substance exhibiting glucagon activity at 0.37 nmol/kg, 0.75 nmol/kg, or 1.12 nmol/kg and the GLP-1 and GIP receptor dual agonist at 10.39 nmol/kg, 20.77 nmol/kg, or 31.16 nmol/kg, but is not limited thereto. The composition of the present invention may comprise the substance exhibiting glucagon activity and the GLP-1 and GIP receptor dual agonist at a molar ratio of 1:0.1 to 1:500, 1:0.5 to 1:250, 1:0.9 to 1:167, or 1:10 to 1:56.2, but is not limited thereto.

However, the dosage of the peptide is determined as the effective dosage for the patient considering various factors such as severity of disease and patient's age, weight, health status, sex, diet, and excretion rate as well as the administration route of the pharmaceutical composition and the number of treatments. In consideration of this point, those of ordinary skill in the art will be able to determine an appropriate effective dosage depending on the specific use of the composition of the present invention. The pharmaceutical composition according to the present invention is not particularly limited in its formulation, administration route and administration method as long as the effect of the present invention is exhibited.

The pharmaceutical composition of the present invention may have excellent in vivo persistence and potency, and may have a lower number and a lower frequency of administration compared to those of other medicaments, but is not particularly limited thereto.

In particular, the pharmaceutical composition of the present invention comprises a glucagon derivative having a changed pI compared to native glucagon as an active ingredient, thus exhibits improved solubility and/or high stability at neutral pH, and thus may be usefully used in the preparation of a stable glucagon formulation for the treatment of a target disease including metabolic syndrome.

In the pharmaceutical composition for the prevention or treatment of metabolic syndrome, therapy for the prevention or treatment of metabolic syndrome, or the like, the pharmaceutical composition may comprise a compound or substance exhibiting therapeutic activity with respect to metabolic syndrome in addition to the substance exhibiting activity with respect to the glucagon receptor and/or the GLP-1 and GIP receptor dual agonist, and the therapy may include further use of the compound or substance.

Another aspect embodying the present invention provides a method for preventing or treating metabolic syndrome, comprising administering a substance exhibiting activity with respect to the glucagon receptor and a GLP-1 and GIP receptor dual agonist to an individual in need thereof.

The substance exhibiting activity with respect to the glucagon receptor, the GLP-1 and GIP receptor dual agonist, the composition comprising these, metabolic syndrome, prevention, and treatment are as described above.

In the present invention, the individual is an individual suspected of metabolic syndrome, and the individual suspected of metabolic syndrome refers to mammals such as mice and livestock, including humans that have or may develop the disease and includes, without limitation, individuals that can be treated with the glucagon derivative and GLP-1 and GIP receptor dual agonist or the composition comprising the same of the present invention. The individual may be efficiently treated by administering the pharmaceutical composition of the present invention to an individual suspected of metabolic syndrome. Metabolic syndrome is as described above.

The method of the present invention may comprise administering a pharmaceutical composition comprising (i) a substance exhibiting activity with respect to the glucagon receptor and (ii) a GLP-1 and GIP receptor dual agonist in a pharmaceutically effective amount. The method according to the present invention may be, but is not limited to, administering (i) the substance exhibiting activity with respect to the glucagon receptor and (ii) the GLP-1 and GIP receptor dual agonist as one preparation, or administering (i) the substance exhibiting activity with respect to the glucagon receptor and (ii) the GLP-1 and GIP receptor dual agonist as separate preparations simultaneously, separately, sequentially, or in reverse order.

A suitable total daily amount may be determined by the treating physician within the scope of sound medical judgment, and may be administered one time or several times by being divided into several doses. However, for the purposes of the present invention, a specific therapeutically effective amount for a specific patient is preferably applied differently depending on various factors and similar factors well known in the medical field, including the kind and extent of the response to be achieved, the specific composition including whether other preparations are optionally used, patient's age, weight, general health, sex and diet, administration time, administration route, secretion rate of composition, treatment period, and drugs used together or simultaneously with the specific composition.

Specifically, the substance exhibiting activity with respect to the glucagon receptor and the GLP-1 and GIP receptor dual agonist may be each administered at about 0.0001 mg to 500 mg per 1 kg of the patient's body weight per day. When the two substances are used in combination, the total amount thereof administered may be about 0.0001 mg to 1000 mg per 1 kg of the patients body weight per day, but the amount administered is not limited thereto.

The substance exhibiting activity with respect to the glucagon receptor and the GLP-1 and GIP receptor dual agonist administered in combination may be administered at a molar ratio of 1:0.01 to 1:100, but the molar ratio is not limited thereto.

Specifically, the substance exhibiting glucagon activity may be administered at 0.15 nmol/kg to 2.5 nmol/kg, 0.19 nmol/kg to 2.25 nmol/kg, 0.25 nmol/kg to 1.5 nmol/kg, or 0.37 nmol/kg to 1.12 nmol/kg, and the GLP-1 and GIP receptor dual agonist may be administered at 2.0 nmol/kg to 35 nmol/kg, 2.08 nmol/kg to 31.16 nmol/kg, or 10.39 nmol/kg to 31.16 nmol/kg, and more specifically, the substance exhibiting glucagon activity may be administered at 0.37 nmol/kg, 0.75 nmol/kg, or 1.12 nmol/kg, and the GLP-1 and GIP receptor dual agonist may be administered at 10.39 nmol/kg, 20.77 nmol/kg, or 31.16 nmol/kg, but the amount administered is not limited thereto. The substance exhibiting glucagon activity and the GLP-1 and GIP receptor dual agonist may be administered at a molar ratio of 1:0.1 to 1:500, 1:0.5 to 1:250, 1:0.9 to 1:167, or 1:10 to 1:56.2, but the molar ratio is not limited thereto.

Although not particularly limited thereto, the method for preventing or treating metabolic syndrome may be a combination therapy further comprising administering a compound or substance exhibiting therapeutic activity with respect to one or more metabolic syndromes in addition to (i) the substance exhibiting activity with respect to the glucagon receptor and (ii) the GLP-1 and GIP receptor dual agonist.

Another aspect embodying the present invention provides the use of a composition comprising (i) a substance exhibiting activity with respect to the glucagon receptor and (ii) a GLP-1 and GIP receptor dual agonist for the prevention or treatment of metabolic syndrome.

Another aspect embodying the present invention provides the use of a composition comprising (i) a substance exhibiting activity with respect to the glucagon receptor and (ii) a GLP-1 and GIP receptor dual agonist for the preparation of a medicament for preventing or treating metabolic syndrome.

Hereinafter, the present invention will be described in more detail through Examples. However, these Examples are for illustrative purposes of the present invention, and the scope of the present invention is not limited to these Examples.

Example 1: Production of Cell Line Showing cAMP Response to Glucagon

PCR was performed using the portion corresponding to the ORF in the cDNA of the human glucagon receptor gene (OriGene Technologies, Inc. USA) as a template and a forward primer and a reverse primer of SEQ ID NO: 48 and SEQ ID NO: 49 including the EcoRI cleavage site and the XhoI cleavage site, respectively.

At this time, the PCR reaction of denaturation at 95° C. for 60 seconds, annealing at 55° C. for 60 seconds, and elongation at 68° C. for 30 seconds was repeated 30 times. The PCR product thus amplified was electrophoresed on a 1.0% agarose gel and then obtained by eluting a 450 bp band.

```
Forward primer (SEQ ID NO: 48):
5'-CAGCGACACCGACCGTCCCCCCGTACTTAAGGCC-3'

Reverse primer (SEQ ID NO: 49):
5'-CTAACCGACTCTCGGGGAAGACTGAGCTCGCC-3'
```

The PCR product was cloned into x0GC/dhfr, a known animal cell expression vector, to prepare a recombinant vector x0GC/GCGR.

The recombinant vector x0GC/GCGR thus prepared was transformed into CHO DG44 cells cultured in DMEM/F12 medium containing 10% FBS using lipofectamine, and selectively cultured in a selective medium containing 1 mg/mL G418 and 10 nM methotrexate. From this, monoclonal cell lines were selected by limiting dilution. Among these, cell lines showing excellent concentration-dependent cAMP response to glucagon were finally selected.

Example 2: Synthesis of Glucagon Derivative

In order to develop a glucagon derivative exhibiting improved physical properties, the amino acid sequence of native glucagon of SEQ ID NO: 1 was substituted with negatively and positively charged amino acid residues to synthesize glucagon derivatives as presented in Table 1 below. The relative in vitro activity described herein was measured by way of the method described in Example 4 below.

TABLE 1

Amino add sequences of native glucagon and glucagon derivatives

| SEQ ID NO | Peptide sequence | Presence or absence of ring formation | pl | In vitro activity (relative activity to SEQ ID NO: 1, %) |
|---|---|---|---|---|
| SEQ ID NO: 1 | HSQGTFTSDYSKYLDSRRAQDFVQWLMNT | — | 6.8 | 100 |
| SEQ ID NO: 2 | HSQGTFTSDYSKYLDCDRAQDFVQWLMNT | — | 4.56 | 0.6 |
| SEQ ID NO: 3 | HSQGTFTSDYSKYLDCERAQDFVQWLMNT | — | 4.66 | 6.1 |
| SEQ ID NO: 4 | HSQGTFTSDYSKYLDSCDAQDFVQWLMNT | — | 4.13 | <0.1 |
| SEQ ID NO: 5 | HSQGTFTSDYSKYLDSCEAQDFVQWLMNT | — | 4.22 | 0.3 |
| SEQ ID NO: 6 | HSQGTFTSDYSKYLDSCEADDFVQWLMNT | — | 4.03 | <0.1 |
| SEQ ID NO: 7 | YSQGTFTSDYSKYLDSCEADDFVQWLMNT | — | 3.71 | <0.1 |
| SEQ ID NO: 8 | YXQGTFTSDYSKYLDSCDAQDFVQWLINT | — | 3.77 | <0.1 |
| SEQ ID NO: 9 | YXQGTFTSDYSKYLDSCDAQDFVVWLINT | — | 3.77 | <0.1 |
| SEQ ID NO: 10 | YXQGTFTSDYSKYLDSCDADDFVVWLINT | — | 3.66 | <0.1 |
| SEQ ID NO: 11 | YXQGTFTSDYSKYLDEKCAKEFVQWLMNT | — | 4.78 | 4.6 |
| SEQ ID NO: 12 | YXQGTFTSDYSKYLDEKRAKEFVQWLMNTC | Ring formed | 6.20 | 56.3 |
| SEQ ID NO: 13 | YXQGTFTSDYSCYLDSRRAQDFVQWLMNT | — | 4.43 | 5.2 |
| SEQ ID NO: 14 | YXQGTFTSDYSKYLDCKRAKEFVQWLMNT | — | 8.12 | 18.1 |
| SEQ ID NO: 15 | YXQGTFTSDYSKYLCEKRAQDFVWWLMNT | — | 6.11 | 1.1 |
| SEQ ID NO: 16 | YXQGTFTSDYSKYLDCRRAQVFVQWLMRT | — | 9.11 | 4.2 |
| SEQ ID NO: 17 | YXQGTFTSDYSKYLDCVRAQDFVQWLMRT | — | 6.03 | 23.2 |
| SEQ ID NO: 18 | YXQGTFTSDYSKYLDSRRACDFRLWLMNT | — | 8.15 | <0.1 |
| SEQ ID NO: 19 | YXQGTFTSDYSKYLCEKRAKEFVQWLMNT | Ring formed | 8.12 | 12.1 |
| SEQ ID NO: 20 | YXQGTFTSDYSKYLDECRAKEFVQWLMNT | Ring formed | 4.78 | 299.7 |
| SEQ ID NO: 21 | YXQGTFTSDYSKYLDEKCAKEFVQWLMNT | Ring formed | 4.78 | 57.8 |
| SEQ ID NO: 22 | YXQGTFTSDYSKYLDEKRCKEFVQWLMNT | Ring formed | 6.20 | 147.8 |
| SEQ ID NO: 23 | YXQGTFTSDYSKYCDEKRAKEFVQWLMNT | Ring formed | 6.20 | 76.8 |
| SEQ ID NO: 24 | YXQGTFTSDYSKCLDEKRAKEFVQWLMNT | Ring formed | 6.21 | 58.0 |
| SEQ ID NO: 25 | YXQGTFTSDYSKYLDEKRAKCFVQWLMNT | Ring formed | 8.12 | 46.9 |
| SEQ ID NO: 26 | WXQGTFTSDYSKYLDECRAKDFVQWLMNT | Ring formed | 4.68 | 1.0 |

TABLE 1-continued

Amino add sequences of native glucagon and glucagon derivatives

| SEQ ID NO | Peptide sequence | Presence or absence of ring formation | pl | In vitro activity (relative activity to SEQ ID NO: 1, %) |
|---|---|---|---|---|
| SEQ ID NO: 27 | YXQGTFVSDYSKYLDECRAKDFVQWLMNT | Ring formed | 4.68 | 93.6 |
| SEQ ID NO: 28 | WXQGTFVSDYSKYLDECRAKDFVQWLMNT | Ring formed | 4.68 | <0.1 |
| SEQ ID NO: 29 | YXQGTFTSDYSKCLDERRAKDFVQWLMNT | Ring formed | 6.15 | 61.3 |
| SEQ ID NO: 30 | WXQGTFTSDYSKCLDERRAKDFVQWLMNT | Ring formed | 4.44 | 0.3 |
| SEQ ID NO: 31 | YXQGTFTSDYSKYLDCKRAKEFVQWLMNT | Ring formed | 8.12 | 6.3 |
| SEQ ID NO: 32 | -SQGTFTSDYSKYLDECRAKEFVQWLMNT | Ring formed | 4.78 | 0.7 |
| SEQ ID NO: 33 | YXQGTFTSDYSKYLDSRRAQDFVQWLMNT | — | 6.04 | 108.2 |
| SEQ ID NO: 34 | WXQGTFTSDYSKYCDERRAKEFVQWLMNT | Ring formed | 6.21 | 0.2 |
| SEQ ID NO: 35 | YXQGTFTSDYSKYCDERRAKEFVQWLMNT | Ring formed | 6.2 | 17.7 |
| SEQ ID NO: 36 | YXQGTFTSDCSKYLDERRAKEFVQWLMNT | Ring formed | 6.21 | 9.9 |
| SEQ ID NO: 37 | YXQGTFTSDYSKYLDERRAKEFVQWLMNTC | Ring formed | 6.21 | 225.5 |
| SEQ ID NO: 38 | YXQGTFCSDYSKYLDERRAKEFVQWLMNT | Ring formed | 6.15 | 167.3 |
| SEQ ID NO: 39 | YXQGTFVSDCSKYLDERRAKDFVQWLMNT | Ring formed | 6.15 | 3.7 |
| SEQ ID NO: 40 | YXQGTFVSDYSKYLDERRAKDFVQWLMNTC | Ring formed | 6.15 | 40.8 |
| SEQ ID NO: 41 | YXQGTFCSDYSKYLDERRAKDFVQWLMNT | Ring formed | 6.03 | 45.2 |
| SEQ ID NO: 42 | YXQGTFCSDYSKYLDSRRAQDFVQWLMNT | — | 6.03 | 37.9 |
| SEQ ID NO: 43 | YXQGTFTSDCSKYLDSRRAQDFVQWLMNT | — | 6.03 | 1.6 |
| SEQ ID NO: 44 | YXQGTFTSDYSKYLDSRRAQDFVQWLMNTC | — | 6.21 | 75.4 |
| SEQ ID NO: 45 | YXQGTFTSDYSCYLDEKRAKEFVQWLMNT | — | 4.78 | 5.2 |

The amino acid denoted by X in the sequence presented in Table 1 represents aminoisobutyric acid (Aib), which is a non-natural amino acid, underlines under amino acid symbols indicate the formation of a lactam ring between the side chains of the corresponding underlined amino acid pair, and "-" indicates that there is no amino acid residue at that position. In the column for the presence or absence of ring formation. "-" indicates that no ring is formed in that sequence.

Example 3: Measurement of pI of Glucagon Derivative

In order to verify the improved physical properties of the glucagon derivatives synthesized in Example 2, the pI was estimated from the amino acid sequences using the pI/Mw tool (expasy.org/tools/pi_tool.html; Gasteiger et al., 2003) on the ExPASy server.

As presented in Table 1 above, the native glucagon of SEQ ID NO: 1 had a pI of 6.8, while some glucagon derivatives according to the present invention had a pI in a range of about 4 to 6. These glucagon derivatives have a pI lower or higher than that of native glucagon, and thus may exhibit improved solubility and higher stability compared to native glucagon at neutral pH and the like.

The patient adherence may be increased when such glucagon derivatives according to the present invention are used as a therapeutic agent for a target disease such as metabolic syndrome, and these glucagon derivatives are suitable for combined administration with other anti-obesity or diabetes drugs and can be usefully used as a therapeutic agent for metabolic syndrome including obesity, diabetes, non-alcoholic steatohepatitis (NASH), dyslipidemia, and coronary heart disease.

Example 4: Measurement of cAMP Activity of Glucagon Derivative

In the cell lines having the human glucagon receptor produced in Example 1, the activity of the glucagon derivatives synthesized in Example 2 was measured. Specifically, the transformed cell lines were subcultured 3 or 4 times a week, and then the subcultured cell lines were seeded in a 384-well plate by $6\times10^3$ per well and cultured for 24 hours. In HBSS (Hank's balanced salt solution) buffer containing 0.5 mM IBMX (3-isobutyl-1-methylxanthine), 0.1% BSA (bovine serum albumin), and 5 mM HEPES (4-(2-hydroxyethyl)-1-piperazineethanesulfonic acid), native glucagon was suspended at 200 nM and the glucagon derivative at 1600 nM, and then serially diluted 4-fold 10 times. This was applied to the cAMP assay kit (LANCE cAMP 384 kit, PerkinElmer) and added to the cultured cell lines, and then the fluorescence value was measured. After the measurement, the highest fluorescence value was selected as 100%. $EC_{50}$ values of glucagon derivatives were calculated from this, and the values were compared with that of native glucagon. The results are presented in Table 1 above.

Example 5: Preparation of Conjugate Comprising Glucagon Derivative and Immunoglobulin Fc (Glucagon Derivative-Immunoglobulin Fc Region Conjugate)

As a representative glucagon derivative, glucagon derivatives with a pI value of 6 to 7 and in vitro activity of 200% or more prepared in Example 2 were selected to prepare conjugates. Specifically, for pegylation of PEG of 10 kDa having a maleimide group and an aldehyde group at both terminuses, respectively, namely maleimide-PEG-aldehyde (10 kDa, NOF, Japan) to the cysteine residue of glucagon derivative, the molar ratio of the glucagon derivative to maleimide-PEG-aldehyde was set to 1:1 to 5, and the protein concentration was set to 3 mg/mL to 10 mg/mL, and the reaction was conducted at low temperature for 1 to 3 hours. At this time, the reaction was conducted in an environment in which 20% to 60% isopropanol was added to 50 mM Tris buffer (pH 7.5). After the reaction was completed, the reaction solution was applied to SP sepharose HP (GE Healthcare, USA) to purify a glucagon derivative mono-pegylated to cysteine.

Next, the purified mono-pegylated glucagon derivative and immunoglobulin Fc (homodimer of SEQ ID NO: 71) were reacted at 4° C. to 8° C. for 12 to 18 hours by setting the molar ratio to 1:2 to 10 and the protein concentration to 10 mg/mL to 50 mg/mL. The reaction was conducted in an environment in which 10 mM to 50 mM sodium cyanoborohydride and 10% to 20% isopropanol as reducing agents were added to 100 mM potassium phosphate buffer (pH 6.0). After the reaction was completed, the reaction solution was applied to the Butyl sepharose FF purification column (GE Healthcare, USA) and the Source ISO purification column (GE Healthcare, USA) to purify a conjugate comprising a glucagon derivative and immunoglobulin Fc.

In the immunoglobulin Fc, two monomers having the amino acid sequence of SEQ ID NO: 71 (consisting of 221 amino acids) form a homodimer through an inter-disulfide bond between cysteines, the third amino acid of each monomer, and a disulfide bond between cysteines at positions 35 and 95 and a disulfide bond between cysteines at positions 141 and 199 are independently formed in each of the monomers of the homodimer.

The purity analyzed by reverse phase chromatography, size-exclusion chromatography, and ion-exchange chromatography after preparation was 95% or more.

Here, the conjugate in which a glucagon derivative and immunoglobulin Fc are linked via PEG was named "glucagon derivative long-acting conjugate" or "long-acting glucagon derivative", and these may be used interchangeably herein.

Example 6: Production of Cell Line Showing cAMP Response to GLP-1 and GIP

A recombinant vector was constructed using the expression vector X0GC/dhfr so as to express human GLP-1 receptor and human GIP receptor, then transformed into CHO DG44 cells using lipofectamine, and selectively cultured in a selective medium containing G418 and methotrexate. From this, monoclonal cell lines were selected by limiting dilution. Among these, cell lines showing excellent concentration-dependent cAMP response to GLP-1 and GIP were finally selected.

Example 7: Preparation of Acylated GLP-1 and GIP Receptor Dual Agonist

Tirzepatide, a dual agonist that exhibited activity with respect to both the GLP-1 receptor and the GIP receptor, was synthesized, and the preparation method thereof was performed with reference to a known method (WO 2016-111971 A1).

Example 8: Measurement of cAMP Activity of Acylated GLP-1 and GIP Receptor Dual Agonist In the cell lines expressing human GLP-1 receptor and human GIP receptor produced in Example 6, the activity of the dual agonist synthesized in Example 7 was measured.

Specifically, the transformed cell lines of Example 6 were subcultured 3 or 4 times a week, and then the subcultured cell lines were seeded in a 384-well plate by $6\times10^3$ per well and cultured for 24 hours. In HBSS (Hank's balanced salt solution) buffer containing 0.5 mM IBMX (3-isobutyl-1-methylxanthine), 0.1% BSA (bovine serum albumin), and 5 mM HEPES (4-(2-hydroxyethyl)-1-piperazineethanesulfonic acid), native GLP-1 and GIP were suspended at 200 nM and the dual agonist at 1600 nM, and then serially diluted 4-fold 10 times. This was applied to the cAMP assay kit (LANCE cAMP 384 kit, PerkinElmer) and added to each of the cultured cell lines, and then the fluorescence value was measured. Thereafter, the fluorescence value of the native substance at the highest concentration used in each cell line was selected as 100%, $EC_{50}$ value of the dual agonist was calculated from this, and the value was compared with those of native GLP-1 and GIP. The results are presented in Table 2 below.

TABLE 2

| Test substance | Relative in vitro activity to native ligand ($EC_{50}$) | |
|---|---|---|
| | GLP-1 receptor | GIP receptor |
| Dual agonist (tirzepatide) | 1.3% | 6.7% |

Experimental Example 1: Comparison of Effect of Long-Acting Glucagon Derivative and Dual Agonist on Body Weight and Fat Weight Loss, Blood Lipid Level Improvement, Insulin Sensitivity Improvement, and Increase in Energy Metabolism-Related Gene Expression in High-Fat Diet-Induced Obese Mice and Verification of Additional Effect Due to Combined Administration A high-fat diet-induced obese mouse, which was widely used as an obese animal model, was used for this study. The body weight of the mice was about 50 g to 55 g before administration. During the study period, seven mice were housed and had free access to water. The lights were turned off from 6 P.M. to 6 A.M.

In the test groups fed with a high-fat diet, group 1 was administered with a vehicle that did not contain a long-acting glucagon derivative (5 mL/kg, injected once every two days)—control group (vehicle), group 2 was administered with GLP-1 analogue anti-obesity drug Saxenda® at 50 nmol/kg (injected twice a day), group 3 was administered with a long-acting glucagon derivative at 2.0 nmol/kg (injected once every two days), group 4 was administered with the dual agonist (tirzepatide) at 20 nmol/kg (injected once every two days), and group 5 was administered with the dual agonist at 20 nmol/kg (injected once every two days) and a long-acting glucagon derivative at 2.0 nmol/kg (injected once every two days) in combination. The administration was performed by subcutaneous injection in all cases.

The experiment was terminated on the 21st day, the changes in body weight of the mice corresponding to each group were measured every two days during the experiment. After the experiment was terminated, the fat weight, blood lipid levels, HOMA-IR, and energy metabolism-related gene expression in tissues were measured.

As a result of measuring the changes in body weight, as can be seen from FIG. 1, the body weights in the long-acting glucagon derivative (2.0 nmol/kg, administered once every two days) single administration group and the long-acting glucagon derivative (2.0 nmol/kg, administered once two days) and dual agonist (tirzepatide) (20 nmol/kg, injected once every two days) combined administration group changed by −34.92% and −51.16% compared to those before administration, respectively. The body weight loss effect was higher in the combined administration group than in the long-acting glucagon derivative single administration group, and this effect was superior to the body weight loss effects of 2.22%, −14.73%, and −19.39% in the control group (vehicle), the GLP-1 analogue anti-obesity drug Saxenda®, and the dual agonist (tirzepatide).

As can be seen from FIGS. 2(A) and 2(B), it was confirmed that the fat weight and blood lipid levels were significantly reduced together with the body weight loss. It was confirmed from the HOMA-IR measurement results that the insulin sensitivity was also improved, as illustrated in FIG. 3(A). Furthermore, an increase in the expression of energy metabolism-related genes (UCP-1, a marker related to thermal energy production, and PGC-1α, a marker related to mitochondrial biosynthesis) in adipose tissue was also confirmed, as illustrated in FIG. 3(B).

Experimental Example 2: Effect of Long-Acting Glucagon Derivative and Dual Agonist on NASH and Fibrosis Improvement in Mouse with NASH and Fibrosis Induced by Choline-Deficient and High-Fat, High-Cholesterol Diet In order to verify the efficacy on NASH and fibrosis improvement by combined administration of the long-acting glucagon derivative and GLP-1/GIP dual agonist (tirzepatide) according to the present invention prepared in Examples, a CD-HFD (choline-deficient and high-fat, high-cholesterol diet) mouse model was used.

Mice induced by 8-week CD-HFD were divided into a vehicle control group, a long-acting glucagon derivative (1.3 nmol/kg, Q2D, subcutaneous) administration group, a dual agonist (73 nmol/kg, Q2D, subcutaneous) administration group, and a long-acting glucagon derivative and dual agonist combined administration group, and repeated administration was performed for 6 weeks. As a negative control group, a group administered with a vehicle to normal diet mice was used. After 6 weeks of repeated administration, the liver tissue of each mouse was taken as an autopsy, and the efficacy on NASH and fibrosis improvement was evaluated by measuring NAS (NAFLD activity score) through H&E staining and collagen expression through quantitative PCR.

As a result, it was confirmed that when a long-acting glucagon derivative or dual agonist was administered repeatedly for 6 weeks, NAS was significantly reduced compared to the CD-HFD diet, vehicle control group.

Furthermore, it was confirmed that when the long-acting glucagon derivative and the dual agonist were administered in combination, the additional NAS reduction was significant (FIG. 4), and it was thus confirmed that the efficacy of the long-acting glucagon derivative and the GLP-1/GIP dual agonist on NASH improvement could be further enhanced through combined administration.

In addition, collagen expression in liver tissue increased in the CD-HFD diet, vehicle control group was significantly reduced by administration of the long-acting glucagon derivative or dual agonist, and this reduction was also confirmed to be further enhanced through combined administration of the long-acting glucagon derivative and the dual agonist (FIG. 5).

It was confirmed that excellent efficacy on NASH and liver fibrosis improvement could be obtained in CD-HFD mice by the combined administration of a long-acting glucagon derivative and a GLP-1/GIP dual agonist through the effect on reduction in NAS and collagen expression in liver tissue.

For the statistical processing in all the cases, the vehicle group (control group) and the test groups were compared using one-way ANOVA, and the t-test was used to compare the additional efficacy of the combined administration group with that of the single administration group (* to ** $p<0.05$ to 0.001 vs. vehicle control group).

These results suggest that a long-acting glucagon derivative exhibits a higher body weight loss effect than a single GLP-1 analogue and a single dual agonist, which are other anti-obesity drugs. Furthermore, when a long-acting glucagon derivative is administered in combination with a GLP-1 and GIP receptor dual agonist, it has been confirmed that not only can the enhanced effect on obesity treatment through additional body weight loss be expected, but also the effect on blood sugar improvement through insulin sensitivity improvement can be expected. Together with these effects of improving obesity and blood sugar, it has been confirmed that excellent effects on liver diseases such as non-alcoholic steatohepatitis or liver fibrosis resulting therefrom can be obtained through reduction in NAS and collagen expression in liver tissue when a long-acting glucagon derivative and a GLP-1 and GIP receptor dual agonist are administered in combination.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims or equivalents of such metes and bounds are therefore intended to be embraced by the claims.

The invention claimed is:

1. A method for treating metabolic syndrome in a subject in need thereof, comprising administering a pharmaceutical composition comprising (i) a substance exhibiting activity with respect to a glucagon receptor and (ii) a Glucagon-like peptide-1 (GLP-1) and glucose-dependent insulinotropic polypeptide (GIP) receptor dual agonist, in a pharmaceutically effective amount, to the subject, wherein the pharmaceutical composition comprises the substance exhibiting activity with respect to a glucagon receptor and the Glucagon-like peptide-1 (GLP-1) and glucose-dependent insulinotropic polypeptide (GIP) receptor dual agonist at a molar ratio of 1:10 to 1:56.2, wherein the substance exhibiting activity with respect to the glucagon receptor is a peptide comprising the amino acid sequence of SEQ ID NO: 37, wherein the GLP-1 and GIP receptor dual agonist is tirzepatide, wherein the metabolic syndrome is selected from the group consisting of impaired glucose tolerance, dyslipidemia, obesity, diabetes, simple steatosis, non-alcoholic fatty liver (NAFLD), non-alcoholic steatohepatitis (NASH), liver fibrosis, and a combination thereof, and wherein the peptide is in a form of a long-acting conjugate, and the long-acting conjugate is represented by Chemical Formula 1:

X—L—F wherein X is a peptide comprising the amino acid sequence of SEQ ID NO: 37;

L is a linker containing an ethylene glycol repeating unit;

F is an immunoglobulin Fc region; and

— represents linkage between X and L and between L and F by a covalent bond.

2. The method according to claim 1, wherein a C-terminus of the peptide is amidated.

3. The method according to claim 1, wherein the ethylene glycol repeating unit in L has a molecular weight in a range of 1 kDa to 100 kDa.

4. The method according to claim 1, wherein the simple steatosis, non-alcoholic fatty liver (NAFLD), or liver fibrosis is due to or accompanied by non-alcoholic steatohepatitis.

5. The method according to claim 1, wherein the administering the composition performs one or more of the following (a)-(f):

(a) body weight and fat weight loss;

(b) improving blood lipid levels;

(c) improving insulin sensitivity;

(d) reducing UCP-1 (uncoupling protein 1) and PGC-1α (peroxisome proliferator-activated receptor gamma coactivator 1-alpha) gene expression;

(e) reducing NAS (NAFLD activity score); and (f) reducing collagen expression in liver tissue.

6. A method for treating metabolic syndrome in a subject in need thereof, comprising administering to the subject (i) a substance exhibiting activity with respect to a glucagon receptor, and (ii) a GLP-1 and GIP receptor dual agonist, in a pharmaceutically effective amount, to a subject in need thereof, wherein the substance exhibiting activity with respect to a glucagon receptor and the Glucagon-like peptide-1 (GLP-1) and glucose-dependent insulinotropic polypeptide (GIP) receptor dual agonist are administered at a molar ratio of 1:10 to 1:56.2, wherein the substance exhibiting activity with respect to the glucagon receptor is a peptide comprising the amino acid sequence of SEQ ID NO: 37, wherein the GLP-1 and GIP receptor dual agonist is tirzepatide, wherein the metabolic syndrome is selected from the group consisting of impaired glucose tolerance, dyslipidemia, obesity, diabetes, simple steatosis, non-alcoholic fatty liver (NAFLD), non-alcoholic steatohepatitis (NASH), liver fibrosis, and a combination thereof, and wherein the peptide is in a form of a long-acting conjugate, and the long-acting conjugate is represented by Chemical Formula 1:

X—L13 F wherein X is a peptide comprising the amino acid sequence of SEQ ID NO: 37;

L is a linker containing an ethylene glycol repeating unit;

F is an immunoglobulin Fc region; and

— represents linkage between X and L and between L and F by a covalent bond.

* * * * *

SEQUENCE LISTING

<160> NUMBER OF SEQ ID NOS: 71

<210> SEQ ID NO 1
<211> LENGTH: 29
<212> TYPE: PRT
<213> ORGANISM: homo sapiens

<400> SEQUENCE: 1

His Ser Gln Gly Thr Phe Thr Ser Asp Tyr Ser Lys Tyr Leu Asp Ser
1 5 10 15

Arg Arg Ala Gln Asp Phe Val Gln Trp Leu Met Asn Thr
20 25

<210> SEQ ID NO 2
<211> LENGTH: 29
<212> TYPE: PRT
<213> ORGANISM: Artificial Sequence
<220> FEATURE:
<223> OTHER INFORMATION: glucagon derivative

<400> SEQUENCE: 2

His Ser Gln Gly Thr Phe Thr Ser Asp Tyr Ser Lys Tyr Leu Asp Cys
1 5 10 15

Asp Arg Ala Gln Asp Phe Val Gln Trp Leu Met Asn Thr
20 25

<210> SEQ ID NO 3
<211> LENGTH: 29
<212> TYPE: PRT
<213> ORGANISM: Artificial Sequence
<220> FEATURE:
<223> OTHER INFORMATION: glucagon derivative

<400> SEQUENCE: 3

His Ser Gln Gly Thr Phe Thr Ser Asp Tyr Ser Lys Tyr Leu Asp Cys
1 5 10 15

Glu Arg Ala Gln Asp Phe Val Gln Trp Leu Met Asn Thr
20 25

<210> SEQ ID NO 4
<211> LENGTH: 29
<212> TYPE: PRT
<213> ORGANISM: Artificial Sequence
<220> FEATURE:
<223> OTHER INFORMATION: glucagon derivative

<400> SEQUENCE: 4

His Ser Gln Gly Thr Phe Thr Ser Asp Tyr Ser Lys Tyr Leu Asp Ser
1 5 10 15

Cys Asp Ala Gln Asp Phe Val Gln Trp Leu Met Asn Thr
20 25

<210> SEQ ID NO 5
<211> LENGTH: 29
<212> TYPE: PRT
<213> ORGANISM: Artificial Sequence
<220> FEATURE:
<223> OTHER INFORMATION: glucagon derivative

<400> SEQUENCE: 5

His Ser Gln Gly Thr Phe Thr Ser Asp Tyr Ser Lys Tyr Leu Asp Ser
1 5 10 15

Cys Glu Ala Gln Asp Phe Val Gln Trp Leu Met Asn Thr
20 25

<210> SEQ ID NO 6
<211> LENGTH: 29
<212> TYPE: PRT
<213> ORGANISM: Artificial Sequence
<220> FEATURE:
<223> OTHER INFORMATION: glucagon derivative

<400> SEQUENCE: 6

His Ser Gln Gly Thr Phe Thr Ser Asp Tyr Ser Lys Tyr Leu Asp Ser
1 5 10 15

Cys Glu Ala Asp Asp Phe Val Gln Trp Leu Met Asn Thr
20 25

<210> SEQ ID NO 7
<211> LENGTH: 29
<212> TYPE: PRT
<213> ORGANISM: Artificial Sequence
<220> FEATURE:
<223> OTHER INFORMATION: glucagon derivative

<400> SEQUENCE: 7

Tyr Ser Gln Gly Thr Phe Thr Ser Asp Tyr Ser Lys Tyr Leu Asp Ser
1 5 10 15

Cys Glu Ala Asp Asp Phe Val Gln Trp Leu Met Asn Thr
20 25

<210> SEQ ID NO 8
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 8

Tyr Xaa Gln Gly Thr Phe Thr Ser Asp Tyr Ser Lys Tyr Leu Asp Ser
1 5 10 15

Cys Asp Ala Gln Asp Phe Val Gln Trp Leu Ile Asn Thr
20 25

<210> SEQ ID NO 9
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 9

Tyr Xaa Gln Gly Thr Phe Thr Ser Asp Tyr Ser Lys Tyr Leu Asp Ser
1 5 10 15

Cys Asp Ala Gln Asp Phe Val Val Trp Leu Ile Asn Thr
20 25

<210> SEQ ID NO 10
<211> LENGTH: 29
<212> TYPE: PRT
<213> ORGANISM: Artificial Sequence
<220> FEATURE:

-continued

```
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 10

Tyr Xaa Gln Gly Thr Phe Thr Ser Asp Tyr Ser Lys Tyr Leu Asp Ser
1               5                   10                  15

Cys Asp Ala Asp Asp Phe Val Val Trp Leu Ile Asn Thr
            20                  25


<210> SEQ ID NO 11
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 11

Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25


<210> SEQ ID NO 12
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 12

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30


<210> SEQ ID NO 13
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 13

Tyr Xaa Gln Gly Thr Phe Thr Ser Asp Tyr Ser Cys Tyr Leu Asp Ser
1               5                   10                  15

Arg Arg Ala Gln Asp Phe Val Gln Trp Leu Met Asn Thr
            20                  25
```

-continued

```
<210> SEQ ID NO 14
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 14

Tyr Xaa Gln Gly Thr Phe Thr Ser Asp Tyr Ser Lys Tyr Leu Asp Cys
1               5                   10                  15

Lys Arg Ala Lys Glu Phe Val Gln Trp Leu Met Asn Thr
            20                  25


<210> SEQ ID NO 15
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 15

Tyr Xaa Gln Gly Thr Phe Thr Ser Asp Tyr Ser Lys Tyr Leu Cys Glu
1               5                   10                  15

Lys Arg Ala Gln Asp Phe Val Val Trp Leu Met Asn Thr
            20                  25


<210> SEQ ID NO 16
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 16

Tyr Xaa Gln Gly Thr Phe Thr Ser Asp Tyr Ser Lys Tyr Leu Asp Cys
1               5                   10                  15

Arg Arg Ala Gln Val Phe Val Gln Trp Leu Met Arg Thr
            20                  25


<210> SEQ ID NO 17
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 17

Tyr Xaa Gln Gly Thr Phe Thr Ser Asp Tyr Ser Lys Tyr Leu Asp Cys
1               5                   10                  15

Val Arg Ala Gln Asp Phe Val Gln Trp Leu Met Arg Thr
            20                  25
```

-continued

<210> SEQ ID NO 18
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 18

```
Tyr Xaa Gln Gly Thr Phe Thr Ser Asp Tyr Ser Lys Tyr Leu Asp Ser
1               5                   10                  15

Arg Arg Ala Cys Asp Phe Arg Leu Trp Leu Met Asn Thr
            20                  25
```

<210> SEQ ID NO 19
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 19

```
Tyr Xaa Gln Gly Thr Phe Thr Ser Asp Tyr Ser Lys Tyr Leu Cys Glu
1               5                   10                  15

Lys Arg Ala Lys Glu Phe Val Gln Trp Leu Met Asn Thr
            20                  25
```

<210> SEQ ID NO 20
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 20

```
Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Met Asn Thr
            20                  25
```

<210> SEQ ID NO 21
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

```
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 21

Tyr Xaa Gln Gly Thr Phe Thr Ser Asp Tyr Ser Lys Tyr Leu Asp Glu
1               5                   10                  15

Lys Cys Ala Lys Glu Phe Val Gln Trp Leu Met Asn Thr
            20                  25


<210> SEQ ID NO 22
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 22

Tyr Xaa Gln Gly Thr Phe Thr Ser Asp Tyr Ser Lys Tyr Leu Asp Glu
1               5                   10                  15

Lys Arg Cys Lys Glu Phe Val Gln Trp Leu Met Asn Thr
            20                  25


<210> SEQ ID NO 23
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 23

Tyr Xaa Gln Gly Thr Phe Thr Ser Asp Tyr Ser Lys Tyr Cys Asp Glu
1               5                   10                  15

Lys Arg Ala Lys Glu Phe Val Gln Trp Leu Met Asn Thr
            20                  25


<210> SEQ ID NO 24
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 24
```

-continued

```
Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Met Asn Thr
            20                  25


<210> SEQ ID NO 25
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 25

Tyr Xaa Gln Gly Thr Phe Thr Ser Asp Tyr Ser Lys Tyr Leu Asp Glu
1               5                   10                  15

Lys Arg Ala Lys Cys Phe Val Gln Trp Leu Met Asn Thr
            20                  25


<210> SEQ ID NO 26
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 26

Trp Xaa Gln Gly Thr Phe Thr Ser Asp Tyr Ser Lys Tyr Leu Asp Glu
1               5                   10                  15

Cys Arg Ala Lys Asp Phe Val Gln Trp Leu Met Asn Thr
            20                  25


<210> SEQ ID NO 27
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 27

Tyr Xaa Gln Gly Thr Phe Val Ser Asp Tyr Ser Lys Tyr Leu Asp Glu
1               5                   10                  15

Cys Arg Ala Lys Asp Phe Val Gln Trp Leu Met Asn Thr
            20                  25
```

-continued

<210> SEQ ID NO 28
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 28

Trp Xaa Gln Gly Thr Phe Val Ser Asp Tyr Ser Lys Tyr Leu Asp Glu
1 5 10 15

Cys Arg Ala Lys Asp Phe Val Gln Trp Leu Met Asn Thr
20 25

<210> SEQ ID NO 29
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 29

Tyr Xaa Gln Gly Thr Phe Thr Ser Asp Tyr Ser Lys Cys Leu Asp Glu
1 5 10 15

Arg Arg Ala Lys Asp Phe Val Gln Trp Leu Met Asn Thr
20 25

<210> SEQ ID NO 30
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 30

Trp Xaa Gln Gly Thr Phe Thr Ser Asp Tyr Ser Lys Cys Leu Asp Glu
1 5 10 15

Arg Arg Ala Lys Asp Phe Val Gln Trp Leu Met Asn Thr
20 25

<210> SEQ ID NO 31
<211> LENGTH: 29
<212> TYPE: PRT
<213> ORGANISM: Artificial Sequence
<220> FEATURE:
<223> OTHER INFORMATION: glucagon derivative
<220> FEATURE:

-continued

```
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (17)..(21)
<223> OTHER INFORMATION: amino acids at positions 17 and 21 form a ring

<400> SEQUENCE: 31

Tyr Xaa Gln Gly Thr Phe Thr Ser Asp Tyr Ser Lys Tyr Leu Asp Cys
1               5                   10                  15

Lys Arg Ala Lys Glu Phe Val Gln Trp Leu Met Asn Thr
            20                  25


<210> SEQ ID NO 32
<211> LENGTH: 28
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (15)..(19)
<223> OTHER INFORMATION: amino acids at positions 15 and 19 form a ring

<400> SEQUENCE: 32

Ser Gln Gly Thr Phe Thr Ser Asp Tyr Ser Lys Tyr Leu Asp Glu Cys
1               5                   10                  15

Arg Ala Lys Glu Phe Val Gln Trp Leu Met Asn Thr
            20                  25


<210> SEQ ID NO 33
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 33

Tyr Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25


<210> SEQ ID NO 34
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 34

Trp Xaa Gln Gly Thr Phe Thr Ser Asp Tyr Ser Lys Tyr Cys Asp Glu
1               5                   10                  15

Arg Arg Ala Lys Glu Phe Val Gln Trp Leu Met Asn Thr
            20                  25
```

<210> SEQ ID NO 35
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 35

```
Tyr Xaa Gln Gly Thr Phe Thr Ser Asp Tyr Ser Lys Tyr Cys Asp Glu
1               5                   10                  15

Arg Arg Ala Lys Glu Phe Val Gln Trp Leu Met Asn Thr
            20                  25
```

<210> SEQ ID NO 36
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 36

```
Tyr Xaa Gln Gly Thr Phe Thr Ser Asp Cys Ser Lys Tyr Leu Asp Glu
1               5                   10                  15

Arg Arg Ala Lys Glu Phe Val Gln Trp Leu Met Asn Thr
            20                  25
```

<210> SEQ ID NO 37
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 37

```
Tyr Xaa Gln Gly Thr Phe Thr Ser Asp Tyr Ser Lys Tyr Leu Asp Glu
1               5                   10                  15

Arg Arg Ala Lys Glu Phe Val Gln Trp Leu Met Asn Thr Cys
            20                  25                  30
```

<210> SEQ ID NO 38
<211> LENGTH: 29
<212> TYPE: PRT
<213> ORGANISM: Artificial Sequence
<220> FEATURE:

```
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 38

Tyr Xaa Gln Gly Thr Phe Cys Ser Asp Tyr Ser Lys Tyr Leu Asp Glu
1               5                   10                  15

Arg Arg Ala Lys Glu Phe Val Gln Trp Leu Met Asn Thr
            20                  25


<210> SEQ ID NO 39
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 39

Tyr Xaa Gln Gly Thr Phe Val Ser Asp Cys Ser Lys Tyr Leu Asp Glu
1               5                   10                  15

Arg Arg Ala Lys Asp Phe Val Gln Trp Leu Met Asn Thr
            20                  25


<210> SEQ ID NO 40
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 40

Tyr Xaa Gln Gly Thr Phe Val Ser Asp Tyr Ser Lys Tyr Leu Asp Glu
1               5                   10                  15

Arg Arg Ala Lys Asp Phe Val Gln Trp Leu Met Asn Thr Cys
            20                  25                  30


<210> SEQ ID NO 41
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
```

<222> LOCATION: (16)..(20)
<223> OTHER INFORMATION: amino acids at positions 16 and 20 form a ring

<400> SEQUENCE: 41

```
Tyr Xaa Gln Gly Thr Phe Cys Ser Asp Tyr Ser Lys Tyr Leu Asp Glu
1               5                   10                  15

Arg Arg Ala Lys Asp Phe Val Gln Trp Leu Met Asn Thr
            20                  25
```

<210> SEQ ID NO 42
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 42

```
Tyr Xaa Gln Gly Thr Phe Cys Ser Asp Tyr Ser Lys Tyr Leu Asp Ser
1               5                   10                  15

Arg Arg Ala Gln Asp Phe Val Gln Trp Leu Met Asn Thr
            20                  25
```

<210> SEQ ID NO 43
<211> LENGTH: 29
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 43

```
Tyr Xaa Gln Gly Thr Phe Thr Ser Asp Cys Ser Lys Tyr Leu Asp Ser
1               5                   10                  15

Arg Arg Ala Gln Asp Phe Val Gln Trp Leu Met Asn Thr
            20                  25
```

<210> SEQ ID NO 44
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 44

```
Tyr Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Cys
            20                  25                  30
```

<210> SEQ ID NO 45
<211> LENGTH: 29
<212> TYPE: PRT
<213> ORGANISM: Artificial Sequence
<220> FEATURE:
<223> OTHER INFORMATION: glucagon derivative
<220> FEATURE:

<221> NAME/KEY: MISC_FEATURE
<222> LOCATION: (2)
<223> OTHER INFORMATION: Xaa is aminoisobutyric acid (Aib)

<400> SEQUENCE: 45

Tyr Xaa Gln Gly Thr Phe Thr Ser Asp Tyr Ser Cys Tyr Leu Asp Glu
1               5                   10                  15

Lys Arg Ala Lys Glu Phe Val Gln Trp Leu Met Asn Thr
            20                  25

<210> SEQ ID NO 46
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is alpha-methyl-glutamic acid, aminoisobutyric acid (Aib), D-alanine, glycine, Sar (N-methylglycine), serine, or D-serine
<220> FEATURE:
<221> NAME/KEY: MISC_FEATURE
<222> LOCATION: (7)
<223> OTHER INFORMATION: Xaa is threonine, valine, or cysteine
<220> FEATURE:
<221> NAME/KEY: MISC_FEATURE
<222> LOCATION: (10)
<223> OTHER INFORMATION: Xaa is tyrosine or cysteine
<220> FEATURE:
<221> NAME/KEY: MISC_FEATURE
<222> LOCATION: (12)
<223> OTHER INFORMATION: Xaa is lysine or cysteine
<220> FEATURE:
<221> NAME/KEY: MISC_FEATURE
<222> LOCATION: (13)
<223> OTHER INFORMATION: Xaa is tyrosine or cysteine
<220> FEATURE:
<221> NAME/KEY: MISC_FEATURE
<222> LOCATION: (14)
<223> OTHER INFORMATION: Xaa is leucine or cysteine
<220> FEATURE:
<221> NAME/KEY: MISC_FEATURE
<222> LOCATION: (15)
<223> OTHER INFORMATION: Xaa is aspartic acid, glutamic acid, or cysteine
<220> FEATURE:
<221> NAME/KEY: MISC_FEATURE
<222> LOCATION: (16)
<223> OTHER INFORMATION: Xaa is glutamic acid, aspartic acid, serine, alpha-methyl-glutamic acid, or cysteine, or is absent;
<220> FEATURE:
<221> NAME/KEY: MISC_FEATURE
<222> LOCATION: (17)
<223> OTHER INFORMATION: Xaa is aspartic acid, glutamine, glutamic acid, lysine, arginine, serine, cysteine, or valine, or is absent
<220> FEATURE:
<221> NAME/KEY: MISC_FEATURE
<222> LOCATION: (18)
<223> OTHER INFORMATION: Xaa is alanine, aspartic acid, glutamic acid, arginine, valine, or cysteine, or is absent
<220> FEATURE:
<221> NAME/KEY: MISC_FEATURE
<222> LOCATION: (19)
<223> OTHER INFORMATION: Xaa is alanine, arginine, serine, valine, or cysteine, or is absent
<220> FEATURE:
<221> NAME/KEY: MISC_FEATURE
<222> LOCATION: (20)
<223> OTHER INFORMATION: Xaa is lysine, histidine, glutamine, aspartic acid, arginine, alpha-methyl-glutamic acid, or cysteine, or is absent
<220> FEATURE:
<221> NAME/KEY: MISC_FEATURE
<222> LOCATION: (21)

<223> OTHER INFORMATION: Xaa is aspartic acid, glutamic acid, leucine, valine, or cysteine, or is absent
<220> FEATURE:
<221> NAME/KEY: MISC_FEATURE
<222> LOCATION: (23)
<223> OTHER INFORMATION: Xaa is isoleucine, valine, or arginine, or is absent
<220> FEATURE:
<221> NAME/KEY: MISC_FEATURE
<222> LOCATION: (24)
<223> OTHER INFORMATION: Xaa is valine, arginine, alanine, cysteine, glutamic acid, lysine, glutamine, alpha-methyl-glutamic acid, or leucine, or is absent;
<220> FEATURE:
<221> NAME/KEY: MISC_FEATURE
<222> LOCATION: (27)
<223> OTHER INFORMATION: Xaa is isoleucine, valine, alanine, lysine, methionine, glutamine, or arginine, or is absent
<220> FEATURE:
<221> NAME/KEY: MISC_FEATURE
<222> LOCATION: (28)
<223> OTHER INFORMATION: Xaa is glutamine, lysine, asparagine, or arginine, or is absent
<220> FEATURE:
<221> NAME/KEY: MISC_FEATURE
<222> LOCATION: (30)
<223> OTHER INFORMATION: Xaa is cysteine, or is absent

<400> SEQUENCE: 46

```
Tyr Xaa Gln Gly Thr Phe Xaa Ser Asp Xaa Ser Xaa Xaa Xaa Xaa Xaa
1               5                   10                  15

Xaa Xaa Xaa Xaa Xaa Phe Xaa Xaa Trp Leu Xaa Xaa Thr Xaa
            20                  25                  30
```

<210> SEQ ID NO 47
<211> LENGTH: 30
<212> TYPE: PRT
<213> ORGANISM: Artificial Sequence
<220> FEATURE:
<223> OTHER INFORMATION: glucagon derivative
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (7)
<223> OTHER INFORMATION: Xaa is threonine, valine, or cysteine
<220> FEATURE:
<221> NAME/KEY: MISC_FEATURE
<222> LOCATION: (10)
<223> OTHER INFORMATION: Xaa is tyrosine or cysteine
<220> FEATURE:
<221> NAME/KEY: MISC_FEATURE
<222> LOCATION: (12)
<223> OTHER INFORMATION: Xaa is lysine or cysteine
<220> FEATURE:
<221> NAME/KEY: MISC_FEATURE
<222> LOCATION: (15)
<223> OTHER INFORMATION: Xaa is aspartic acid or cysteine
<220> FEATURE:
<221> NAME/KEY: MISC_FEATURE
<222> LOCATION: (16)
<223> OTHER INFORMATION: Xaa is glutamic acid or serine
<220> FEATURE:
<221> NAME/KEY: MISC_FEATURE
<222> LOCATION: (17)
<223> OTHER INFORMATION: Xaa is lysine or arginine
<220> FEATURE:
<221> NAME/KEY: MISC_FEATURE
<222> LOCATION: (20)
<223> OTHER INFORMATION: Xaa is glutamine or lysine
<220> FEATURE:
<221> NAME/KEY: MISC_FEATURE
<222> LOCATION: (21)
<223> OTHER INFORMATION: Xaa is aspartic acid or glutamic acid
<220> FEATURE:
<221> NAME/KEY: MISC_FEATURE
<222> LOCATION: (24)
<223> OTHER INFORMATION: Xaa is valine or glutamine
<220> FEATURE:
<221> NAME/KEY: MISC_FEATURE
<222> LOCATION: (30)
<223> OTHER INFORMATION: Xaa is cysteine or is absent

<400> SEQUENCE: 47

```
Tyr Xaa Gln Gly Thr Phe Xaa Ser Asp Xaa Ser Xaa Tyr Leu Xaa Xaa
1               5                   10                  15

Xaa Arg Ala Xaa Xaa Phe Val Xaa Trp Leu Met Asn Thr Xaa
            20                  25                  30
```

<210> SEQ ID NO 48
<211> LENGTH: 34
<212> TYPE: DNA
<213> ORGANISM: Artificial Sequence
<220> FEATURE:
<223> OTHER INFORMATION: forward primer

<400> SEQUENCE: 48
cagcgacacc gaccgtcccc ccgtacttaa ggcc 34

<210> SEQ ID NO 49
<211> LENGTH: 32
<212> TYPE: DNA
<213> ORGANISM: Artificial Sequence
<220> FEATURE:
<223> OTHER INFORMATION: reverse primer

<400> SEQUENCE: 49
ctaaccgact ctcggggaag actgagctcg cc 32

<210> SEQ ID NO 50
<211> LENGTH: 39
<212> TYPE: PRT
<213> ORGANISM: Artificial Sequence
<220> FEATURE:
<223> OTHER INFORMATION: tirzepatide
<220> FEATURE:
<221> NAME/KEY: MISC_FEATURE
<222> LOCATION: (2)
<223> OTHER INFORMATION: Xaa is 2-methylalanine(Aib)
<220> FEATURE:
<221> NAME/KEY: MISC_FEATURE
<222> LOCATION: (13)
<223> OTHER INFORMATION: Xaa is 2-methylalanine(Aib)
<220> FEATURE:
<221> NAME/KEY: MISC_FEATURE
<222> LOCATION: (20)
<223> OTHER INFORMATION: Xaa is N6-{N-(hydrogen icosanedioyl)-g-Glu-bis[iminobis(ethylenoxy)acetyl]}-Lysine
<220> FEATURE:
<221> NAME/KEY: MISC_FEATURE
<222> LOCATION: (39)
<223> OTHER INFORMATION: Xaa is L-serinamide

<400> SEQUENCE: 50

```
Tyr Xaa Glu Gly Thr Phe Thr Ser Asp Tyr Ser Ile Xaa Leu Asp Lys
1               5                   10                  15

Ile Ala Gln Lys Ala Phe Val Gln Trp Leu Ile Ala Gly Gly Pro Ser
            20                  25                  30

Ser Gly Ala Pro Pro Pro Ser
        35
```

<210> SEQ ID NO 51

<211> LENGTH: 12
<212> TYPE: PRT
<213> ORGANISM: HOMO SAPIENS

<400> SEQUENCE: 51

Glu Ser Lys Tyr Gly Pro Pro Cys Pro Ser Cys Pro
1 5 10

<210> SEQ ID NO 52
<211> LENGTH: 11
<212> TYPE: PRT
<213> ORGANISM: Artificial Sequence
<220> FEATURE:
<223> OTHER INFORMATION: Variant of hinge region

<400> SEQUENCE: 52

Glu Ser Lys Tyr Gly Pro Pro Pro Ser Cys Pro
1 5 10

<210> SEQ ID NO 53
<211> LENGTH: 11
<212> TYPE: PRT
<213> ORGANISM: Artificial Sequence
<220> FEATURE:
<223> OTHER INFORMATION: Variant of hinge region

<400> SEQUENCE: 53

Glu Ser Lys Tyr Gly Pro Pro Cys Pro Ser Pro
1 5 10

<210> SEQ ID NO 54
<211> LENGTH: 10
<212> TYPE: PRT
<213> ORGANISM: Artificial Sequence
<220> FEATURE:
<223> OTHER INFORMATION: Variant of hinge region

<400> SEQUENCE: 54

Glu Ser Lys Tyr Gly Pro Pro Cys Pro Ser
1 5 10

<210> SEQ ID NO 55
<211> LENGTH: 10
<212> TYPE: PRT
<213> ORGANISM: Artificial Sequence
<220> FEATURE:
<223> OTHER INFORMATION: Variant of hinge region

<400> SEQUENCE: 55

Glu Ser Lys Tyr Gly Pro Pro Cys Pro Pro
1 5 10

<210> SEQ ID NO 56
<211> LENGTH: 8
<212> TYPE: PRT
<213> ORGANISM: Artificial Sequence
<220> FEATURE:
<223> OTHER INFORMATION: Variant of hinge region

<400> SEQUENCE: 56

Lys Tyr Gly Pro Pro Cys Pro Ser
1 5

<210> SEQ ID NO 57
<211> LENGTH: 8
<212> TYPE: PRT
<213> ORGANISM: Artificial Sequence
<220> FEATURE:
<223> OTHER INFORMATION: Variant of hinge region

<400> SEQUENCE: 57

Glu Ser Lys Tyr Gly Pro Pro Cys
1 5

<210> SEQ ID NO 58
<211> LENGTH: 7
<212> TYPE: PRT
<213> ORGANISM: Artificial Sequence
<220> FEATURE:
<223> OTHER INFORMATION: Variant of hinge region

<400> SEQUENCE: 58

Glu Lys Tyr Gly Pro Pro Cys
1 5

<210> SEQ ID NO 59
<211> LENGTH: 6
<212> TYPE: PRT
<213> ORGANISM: Artificial Sequence
<220> FEATURE:
<223> OTHER INFORMATION: Variant of hinge region

<400> SEQUENCE: 59

Glu Ser Pro Ser Cys Pro
1 5

<210> SEQ ID NO 60
<211> LENGTH: 5
<212> TYPE: PRT
<213> ORGANISM: Artificial Sequence
<220> FEATURE:
<223> OTHER INFORMATION: Variant of hinge region

<400> SEQUENCE: 60

Glu Pro Ser Cys Pro
1 5

<210> SEQ ID NO 61
<211> LENGTH: 4
<212> TYPE: PRT
<213> ORGANISM: Artificial Sequence
<220> FEATURE:
<223> OTHER INFORMATION: Variant of hinge region

<400> SEQUENCE: 61

Pro Ser Cys Pro
1

<210> SEQ ID NO 62
<211> LENGTH: 10
<212> TYPE: PRT
<213> ORGANISM: Artificial Sequence
<220> FEATURE:
<223> OTHER INFORMATION: Variant of hinge region

<400> SEQUENCE: 62

Glu Ser Lys Tyr Gly Pro Pro Ser Cys Pro
1 5 10

<210> SEQ ID NO 63
<211> LENGTH: 9
<212> TYPE: PRT
<213> ORGANISM: Artificial Sequence
<220> FEATURE:

-continued

<223> OTHER INFORMATION: Variant of hinge region

<400> SEQUENCE: 63

Lys Tyr Gly Pro Pro Pro Ser Cys Pro
1               5

<210> SEQ ID NO 64
<211> LENGTH: 9
<212> TYPE: PRT
<213> ORGANISM: Artificial Sequence
<220> FEATURE:
<223> OTHER INFORMATION: Variant of hinge region

<400> SEQUENCE: 64

Glu Ser Lys Tyr Gly Pro Ser Cys Pro
1               5

<210> SEQ ID NO 65
<211> LENGTH: 8
<212> TYPE: PRT
<213> ORGANISM: Artificial Sequence
<220> FEATURE:
<223> OTHER INFORMATION: Variant of hinge region

<400> SEQUENCE: 65

Glu Ser Lys Tyr Gly Pro Pro Cys
1               5

<210> SEQ ID NO 66
<211> LENGTH: 7
<212> TYPE: PRT
<213> ORGANISM: Artificial Sequence
<220> FEATURE:
<223> OTHER INFORMATION: Variant of hinge region

<400> SEQUENCE: 66

Lys Tyr Gly Pro Pro Cys Pro
1               5

<210> SEQ ID NO 67
<211> LENGTH: 7
<212> TYPE: PRT
<213> ORGANISM: Artificial Sequence
<220> FEATURE:
<223> OTHER INFORMATION: Variant of hinge region

<400> SEQUENCE: 67

Glu Ser Lys Pro Ser Cys Pro
1               5

<210> SEQ ID NO 68
<211> LENGTH: 6
<212> TYPE: PRT
<213> ORGANISM: Artificial Sequence
<220> FEATURE:
<223> OTHER INFORMATION: Variant of hinge region

<400> SEQUENCE: 68

Glu Ser Pro Ser Cys Pro
1               5

<210> SEQ ID NO 69
<211> LENGTH: 4
<212> TYPE: PRT
<213> ORGANISM: Artificial Sequence
<220> FEATURE:
<223> OTHER INFORMATION: Variant of hinge region -continued

```
<400> SEQUENCE: 69

Glu Pro Ser Cys
1


<210> SEQ ID NO 70
<211> LENGTH: 3
<212> TYPE: PRT
<213> ORGANISM: Artificial Sequence
<220> FEATURE:
<223> OTHER INFORMATION: Variant of hinge region

<400> SEQUENCE: 70

Ser Cys Pro
1


<210> SEQ ID NO 71
<211> LENGTH: 221
<212> TYPE: PRT
<213> ORGANISM: homo sapiens

<400> SEQUENCE: 71

Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220
```